(12) United States Patent
Fu et al.

(10) Patent No.: US 9,638,695 B2
(45) Date of Patent: *May 2, 2017

(54) NONINVASIVE DETECTION OF LUNG CANCER USING EXHALED BREATH

(71) Applicant: University of Louisville Research Foundation, Inc., Louisville, KY (US)

(72) Inventors: Xiaoan Fu, Louisville, KY (US); Michael Nantz, Louisville, KY (US); Michael Bousamra, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/471,793

(22) Filed: Aug. 28, 2014

(65) Prior Publication Data

US 2015/0064796 A1    Mar. 5, 2015

Related U.S. Application Data

(60) Provisional application No. 61/871,024, filed on Aug. 28, 2013.

(51) Int. Cl.
  *G01N 33/574* (2006.01)
  *G01N 1/40* (2006.01)
  (Continued)

(52) U.S. Cl.
  CPC ....... *G01N 33/57423* (2013.01); *G01N 1/405* (2013.01); *G01N 33/543* (2013.01);
  (Continued)

(58) Field of Classification Search
  CPC ......... G01N 33/497; G01N 2033/4975; G01N 1/405; G01N 33/57423; G01N 2800/56;
  (Continued)

(56) References Cited

U.S. PATENT DOCUMENTS 8,349,604 B2    1/2013    Mohapatra et al.
8,491,494 B2    7/2013    Kline
(Continued)

FOREIGN PATENT DOCUMENTS

WO    2011049972 A1    4/2011
WO    2011083473 A1    7/2011
WO    2012135277 A1    10/2012

OTHER PUBLICATIONS

Fu et al., "Noninvasive Detection of Lung Cancer Using Exhaled Breath", Cancer Medicine 2014, 3, pp. 174-181.
(Continued)

*Primary Examiner* — Rebecca M Fritchman
(74) *Attorney, Agent, or Firm* — Wood Herron & Evans LLP

(57) ABSTRACT

A non-invasive method of detecting or screening for lung cancer in a subject specimen is provided. The method includes detecting elevated levels of one or more carbonyl-containing volatile organic compounds (VOCs) that are biomarkers for lung cancer in exhaled breath from the subject specimen. The method may further include obtaining exhaled breath from the subject specimen; forming adducts of the carbonyl-containing VOCs with a reactive chemical compound; quantifying the adducts of the carbonyl-containing VOCs to establish a subject value for each of the adducts; and comparing each subject value to a threshold healthy specimen value for each of the adducts of the carbonyl-containing VOCs. One or more subject values at quantities greater than threshold healthy specimen values are also useful for screening for lung cancer in the subject specimen.

22 Claims, 12 Drawing Sheets

(51) Int. Cl.
G01N 33/543 (2006.01)
G01N 33/64 (2006.01)
G01N 33/497 (2006.01)

(52) U.S. Cl.
CPC ....... *G01N 33/57484* (2013.01); *G01N 33/64* (2013.01); *G01N 2033/4975* (2013.01); *G01N 2033/57453* (2013.01)

(58) Field of Classification Search
CPC ................. G01N 33/543; G01N 33/64; G01N 2033/57453; G01N 33/57484
USPC .......................................................... 436/64
See application file for complete search history.

(56) References Cited

U.S. PATENT DOCUMENTS

| 8,597,953 | B2 | 12/2013 | Haick | |
|---|---|---|---|---|
| 2005/0085740 | A1 | 4/2005 | Davis et al. | |
| 2008/0050839 | A1 | 2/2008 | Suslick et al. | |
| 2013/0150261 | A1* | 6/2013 | Haick et al. | 506/12 |
| 2014/0244229 | A1 | 8/2014 | Zhang et al. | |
| 2015/0064796 | A1 | 3/2015 | Fu et al. | |

OTHER PUBLICATIONS

Bousamra et al., "Quantitative Analysis of Exhaled Carbonyl Compounds Distinguishes Benign from Malignant Pulmonary Disease", Journal of Thoracic Cardiovascular Surgery 2014, 148, pp. 1074-1081.
Amann et al., "Lung Cancer Biomarkers in Exhaled Breath", Expert Review of Molecular Diagnostics 2011, 11, pp. 201-217.
Song et al., "Quantitative Breath Analysis of Volatile Organic Compounds of Lung Cancer Patients", Lung Cancer 2010, 67, pp. 227-231.
Bajtarevic et al., "Noninvasive Detection of Lung Cancer by Analysis of Exhaled Breath", BMC Cancer 2009, 9, pp. 348-363.
Fuchs et al., "Breath Gas Aldehydes as Biomarkers of Lung Cancer", International Journal of Cancer 2010, 126, pp. 2663-2670.
Poli et al., "Determination of Aldehydes in Exhaled Breath of Patients with Lung Cancer by Means of On-Fiber-Derivatisation SPME-GC/MS", Journal of Chromatography B 2010, 878, pp. 2463-2651.
Phillips et al., "Detection of Lung Cancer Using Weighted Digital Analysis of Breath Biomarkers", Clinica Chimica Acta 2008, 393, pp. 76-84.
Mazzone et al., "Exhaled Breath Analysis with a Colorimetric Sensor Array for the Identification and Characterization of Lung Cancer", Journal of Thoracic Oncology 2012, 7, pp. 137-142.
Baresh et al., "Classification of Lung Cancer Histology by Gold Nanoparticle Sensors", Nanomedicine: Nanotechnology, Biology and Medicine 2012, 8, 580-589.
Peled et al., "Non-Invasive Breath Analysis of Pulmonary Nodules", Journal of Thoracic Oncology 2012, 7, pp. 1528-1533.
Broza et al., "A Nanomaterial-Based Breath Test for Short-Term Follow-Up After Lung Tumor Resection", Nanomedicine: Nanotechnology, Biology, and Medicine 2013, 9, 15-21.
Lin et al., "Protocol for Collection and HPLC Analysis of Volatile Carbonyl Compounds in Breath", Clinical Chemistry, American Association for Clinical Chemistry 1995, 41, pp. 1028-1032.
Corradi et al., "Aldehydes in Exhaled Breath Condensate of Patients with Chronic Obstructive Pulmonary Disease", American Journal of Respiratory and Critical Care Medicine 2003, 167, pp. 1380-1386.
Wang et al., "Analysis of Low Molecular Weight Compounds by MALDI-FTICR-MS", Journal of Chromatography B: Biomedical Sciences & Applications 2011, pp. 1166-1179.
Fu et al., "A Novel Microreactor Approach for Analysis of Ketones and Aldehydes in Breath", The Analyst 2011, 136, pp. 4662-4666.
Alfeeli et al., "MEMS-Based Multi-Inlet/Outlet Preconcentrator Coated by Inkjet Printing of Polymer Adsorbents", Sensors and Actuators 2008, pp. 24-32.
Biswas et al., "Nucleophilic Cationization Reagents," Tetrahedron Letters 2010, 51, pp. 1727-1729.
Deng et al., "Determination of Acetone in Human Breath by Gas Chromatography-Mass Spectrometry and Solid-Phase Microextraction with On-Fiber Derivatization" Journal of Chromatography B 2004, 810, pp. 269-275.
Rexach et al., "Quantification of O-glycosylation Stoichiometry and Dynamics Using Resolvable Mass Tags", Nature Chemical Biology 2010, 6, pp. 645-651.
Lamos et al., "Relative Quantification of Carboxylic Acid Metabolites by Liquid-Chromatography Mass-Spectrometry Using Isotopic Variants of Cholamine," Anal Chem. 2007, 79, pp. 5143-5149.
Higashi et al. "Determination of Prostatic Androgens in 10 mg of Tissue Using Liquid Chromatography-Tandem Mass Spectrometry with Charged Derivatization," Anal Bioanal Chem 2005, 382, pp. 1035-1043.
European Patent Office, International Search report in related PCT/US2012/030837, dated Jun. 26, 2012, 13 pages.
Li et al., "A Microfabricated Preconcentration Device for Breath Analysis", Sensors and Actuators B: Chemical: International Journal Devoted to Research and Development of Physical and Chemical Transducers, Elsevier S.A, 2012, 7pp. 130-136.
Li et al., "Preconcentration and Analysis of Trace Volatile Carbonyl Compounds", Analytical Chemistry, 2012, 84, pp. 1288-1293.
Hakim et al., "Volatile Organic Compounds of Lung Cancer and Possible Biochemical Pathways", Chemical Reviews 2012, 112, pp. 5949-5966.
Peled et al., Abstract A36: Breath Biomarkers in the Post NLST-era for the Discrimination between Malignant from Benign Pulmonary Nodules 2012, 18, pp. A36.
Fuchs et al., Breath Gas Aldehydes as Biomarkers of Lung Cancer 2010, 126, pp. 2663-2670.
Hanai et al., "Analysis of Volatile Organic Compounds Released from Human Lung Cancer Cells and from the Urine of Tumor-Bearing Mice", 2012, 12, pp. 1-12.
Peng et al., "Diagnosing Lung Cancer in Exhaled Breath Using Gold Nanoparticles", 2009, 4, pp. 669-673.
Steeghs et al., "An Off-Line Breath Sampling and Analysis Method Suitable for Large Screening Studies", Physiological Measurement, Institute for Physics Publishing, Bristol, GB 2007, 28, pp. 503-514.
European Patent Office, International Search Report and Written Opinion in related PCT/US2014/053163, dated Nov. 30, 2015, 15 pages.
European Patent Office, International Search Report and Written Opinion in related PCT/US2016/044753, dated Nov. 8, 2016, 13 pages.
Xu, Yiwen et al.,"Detection and Identification of Breast Cancer Volatile Organic Compounds Biomarkers Using Highly-Sensitive Single Nanowire Array on a Chip" Journal of Biomedical Nanotechnology, vol. 9, No. 7, Jul. 1, 2013, pp. 1164-1172.
Amal, Haitham et al., "Assessment of Ovarian Cancer Conditions from Exhaled Breath" Obstetrical and Gynecological Survey, vol. 70, No. 2, Feb. 1, 2015, pp. 89-91.
Phillips, Michael et al., "Volatile Biomarkers in the Breath of Women with Breast Cancer" Journal of Breath Research, vol. 4, No. 2, Mar. 2, 2010, pp. 026003.
Phillips, Michael et al., "Prediction of Breast Cancer Using Volatile Biomarkers in the Breath" Breast Cancer Research and Treatment, Kluwer Academic Publishers, vol. 99, No. 1, Feb. 24, 2006, pp. 19-21.
Wang, Changsong et al., "Volatile Organic Metabolites Identify Patents with Breast Cancer, Cyclomastopathy, and Mammary Gland Fibroma" Scientific Reports, vol. 4, Jun. 20, 2014, 6 pp.

* cited by examiner

NONINVASIVE DETECTION OF LUNG CANCER USING EXHALED BREATH

CROSS-REFERENCE TO RELATED APPLICATIONS

Pursuant to 37 C.F.R. §1.78(a), this application claims the benefit of and priority to prior filed, co-pending Provisional Application Ser. No. 61/871,024 filed Aug. 28, 2013, which is expressly incorporated herein by reference in its entirety.

GOVERNMENT GRANT SUPPORT CLAUSE

This invention was made with Government support under Grant Award No. 1159829 awarded by the National Science Foundation. The Government has certain rights in this invention.

FIELD OF THE INVENTION

The present invention is directed to non-invasive methods for detecting and screening for cancer, and more particularly to a non-invasive method for detecting and screening for lung cancer disease.

BACKGROUND

Lung cancer is a major cause of death worldwide, but early detection of lung cancer is a key factor for increasing survival rates of lung cancer patients. Currently, CT and bronchoscopy are the principal techniques used for lung cancer detection by identifying pulmonary nodules, which if certain predetermined criteria are met are then invasively biopsied to determine the pathology of the nodule(s). A recent U.S. National Lung Screening trial found that periodic computerized tomography (CT) screening of heavy smokers could reduce lung cancer mortalities by as much as 20%. However, this benefit is offset by the morbidity, cost, and occasional mortality incurred by pursuing nonmalignant pulmonary nodules and adenopathy. Thus, with the advent and increasing acceptance of computerized tomography (CT) scan screening for lung cancer, the importance of distinguishing benign from malignant intrathoracic disease is ever increasing. Accordingly, it is important to develop reliable methods that minimize the diagnostic burden to patients who have no significant disease while expediting treatment in patients who actually have lung cancer.

In recent years, the analysis of exhaled breath has become an international research frontier because of its applicability for noninvasive health diagnoses. Several approaches have been developed to analyze exhaled breath including the use of sensor arrays, proton-transfer reaction mass spectrometry (PTR-MS), selected ion flow tube mass spectrometry (SIFT-MS), and gas chromatography-mass spectrometry (GC-MS), to name a few. Although some VOCs in exhaled breath have been reported as potential lung cancer biomarkers, there has been no clinical adoption of breath analysis methods for diagnosis because of the lack of cancer specific VOC markers for reliably predicting lung cancer disease state.

Moreover, analyzing exhaled breath for cancer-indicating biomarkers, i.e., excreted metabolic products, is a daunting task, insofar as over 1700 endogenous volatile organic compounds (VOCs) have been identified in human breath. Additionally, many of these endogenous VOCs are present in exhaled breath in quantities that are less than the experimental error of the detection methods that are used to detect and/or identify them. For example, many of the VOCs in breath range from only a few parts per trillion (ppt) to a few parts per billion (ppb) concentration; many chemical species in breath samples are at millions-fold higher concentration than prevalent VOCs, such as water vapor and carbon dioxide, which may need to be removed to avoid swamping most analytical instruments. Additionally, breath is a chemically-diverse mixture containing analogue/homologue/isomeric mixtures of alcohols, ketones, and aldehydes, which complicate the identification of disease biomarkers; and VOCs in breath may include non-metabolic constituents, which may introduce false biomarkers in breath analysis.

Thus, in order to efficiently and accurately analyze VOCs in breath so as to detect or identify a disease state, there are multiple hurdles to overcome. The first hurdle to overcome is that of concentrating the VOCs of interest. General approaches to concentrating one or more VOCs of interest from dilute gaseous samples have focused on one of the following: chemical, cryogenic, and adsorptive methods. The second hurdle is identifying specific relationships between biomarker(s) and/or quantities of specific biomarkers, which can be correlated with a high level of certainty to the presence of the disease state, with a low chance of false-negatives.

Therefore, in view of the shortcomings and challenges with conventional methods of detecting/identifying and screening for lung cancer, there is a need for new non-invasive methods.

SUMMARY

Embodiments of the present invention provide a non-invasive method for detecting or screening for lung cancer.

According to one embodiment of the present invention, a non-invasive method of detecting or screening for a lung cancer disease state in a subject specimen is provided. The method includes quantifying levels of one or more carbonyl-containing volatile organic compounds (VOCs) that are biomarkers for lung cancer in exhaled breath from the subject specimen, and diagnosing the subject specimen as having a likelihood of the lung cancer disease state if the level of one or more of the carbonyl-containing VOCs is elevated above its respective threshold healthy specimen value. In one embodiment, the carbonyl-containing VOC is a adduct of a reactive chemical that is formed by a dehydration reaction. The carbonyl-containing VOC biomarker is selected from the group consisting of 2-butanone, 2-hydroxyacetaldehyde, 3-hydroxy-2-butanone, 4-hydroxy-2-hexenal, 4-hydroxy-2-nonenal, and a mixture of $C_5H_{10}O$ compounds, which includes 2-pentanone and pentanal. The number of elevated biomarkers correlates to the likelihood of lung cancer, meaning more elevated biomarkers relates to increased likelihood of lung cancer.

According to another embodiment, a method of screening for a lung cancer disease state in a subject specimen is provided, the method comprises the steps of: obtaining exhaled breath from the subject specimen, wherein the exhaled breath includes a plurality of carbonyl-containing volatile organic compounds (VOCs); forming adducts of the plurality of carbonyl-containing VOCs with a reactive chemical compound; quantifying each of the adducts of each of the plurality of carbonyl-containing VOCs to establish a subject value for each of the adducts; and comparing each subject value to a threshold healthy specimen value for each of the adducts of the plurality of carbonyl-containing VOCs, the threshold healthy specimen value corresponding to values calculated from healthy specimens, in order to determine the presence of one or more subject values at quantities greater than their respective range of healthy specimen values, thereby indicating a substantial likelihood of a lung cancer disease state in the subject specimen. Exemplary types of lung cancer suitable for detection using the methods described herein include, but are not limited to small cell lung cancer (SCLC), non-small cell lung cancer (NSCLC), squamous cell carcinoma, and adenocarcionoma. In other embodiments, two or more, or three or more, or four or more subject values are elevated above their respective healthy specimen values.

In accordance with another embodiment, a non-invasive method of detecting a lung cancer disease state in a subject specimen is provided, the method comprising the steps of: concentrating a plurality of carbonyl-containing volatile organic compounds (VOCs) contained in exhaled breath obtained from the subject specimen, wherein the plurality of carbonyl-containing VOCs is selected from the group consisting of 2-butanone, 2-hydroxyacetaldehyde, 3-hydroxy-2-butanone, 4-hydroxy-2-hexenal, 4-hydroxy-2-nonenal, and a mixture of $C_5H_{10}O$ compounds, which includes 2-pentanone and pentanal, which form adducts with a reactive chemical compound; quantifying the adducts of the plurality of carbonyl-containing VOCs to establish a subject value for each member of the adducts of the plurality of carbonyl-containing VOCs; and comparing the subject value for each member of the adducts of the plurality of carbonyl-containing VOCs to a threshold healthy specimen value for each member of the adducts of the plurality of carbonyl-containing VOCs to determine the presence of one or more subject values at quantities greater than its respective threshold healthy specimen value thereby indicating a substantial likelihood of the lung cancer disease state in the subject specimen. In another embodiment, two or more, or three or more, or four or more subject values are elevated above their respective healthy specimen values. In another embodiment, the plurality of carbonyl-containing VOCs is selected from the group consisting of 2-butanone, 2-hydroxyacetaldehyde, 3-hydroxy-2-butanone, and 4-hydroxy-2-hexenal.

In accordance with another embodiment, various types of lung cancer may be distinguished by quantifying 4-hydroxy-2-nonenal and/or a mixture of $C_5H_{10}O$ compounds, which includes 2-pentanone and pentanal, in exhaled breath, and/or staging of the cancerous disease state may be indicated by quantifying 2-butanone in exhaled breath, as described in more details below.

BRIEF DESCRIPTION OF THE DRAWINGS

The accompanying drawings, which are incorporated in and constitute a part of this specification, illustrate embodiments of the invention and, together with the general description of the invention given above, and the detailed description given below, serve to describe the invention.

DETAILED DESCRIPTION OF EMBODIMENTS OF THE INVENTION

Figure 1:
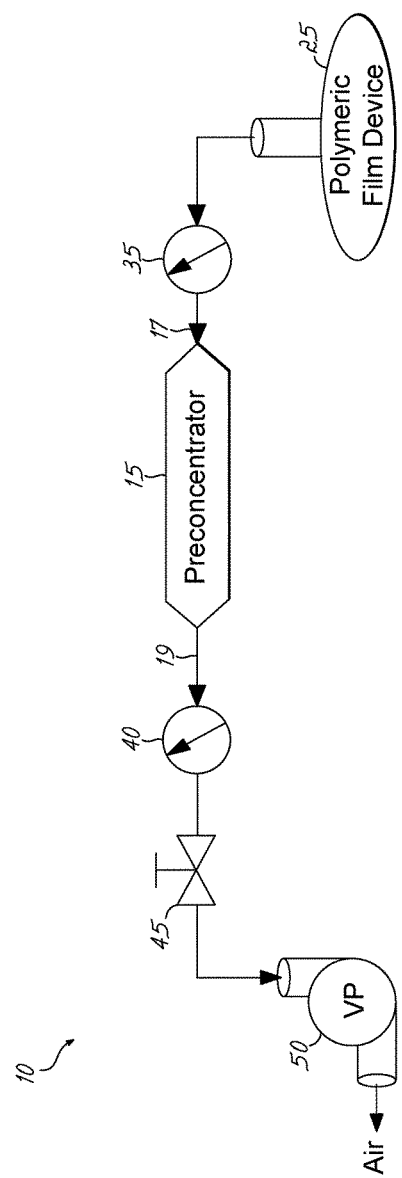
FIG. 1 is a schematic setup for concentrating carbonyl-containing VOCs in an air sample or a gaseous breath sample, in accordance with an embodiment of the present invention.

According to one embodiment of the present invention, a method of detecting or screening for a lung cancer disease state in a subject specimen is provided.

In one embodiment, the method includes detecting levels of one or more carbonyl-containing volatile organic compounds (VOCs) that are biomarkers for lung cancer in exhaled breath from the subject specimen, and diagnosing the subject specimen as having a likelihood of the lung cancer disease state if the level of one or more of the carbonyl-containing VOCs is elevated above its respective threshold healthy specimen value. In a preferred embodiment, adducts of the carbonyl-containing VOCs are analyzed. The adducts are formed by a dehydration reaction with a reactive chemical and advantageously permit the carbonyl-containing VOCs in exhaled breath to be preconcentrated prior to analytical testing. In accordance with embodiments of the present invention, the carbonyl-containing VOC biomarker is selected from the group consisting of 2-butanone, 2-hydroxyacetaldehyde, 3-hydroxy-2-butanone, 4-hydroxy-2-hexenal, 4-hydroxy-2-nonenal, and a mixture of $C_5H_{10}O$ compounds, which includes 2-pentanone and pentanal. The number of elevated biomarkers correlates to the likelihood of lung cancer, meaning more elevated biomarkers relates to increased likelihood of lung cancer.

In another embodiment, the method includes the steps of: obtaining exhaled breath from the subject specimen, wherein the exhaled breath includes a plurality of carbonyl-containing volatile organic compounds (VOCs); forming adducts of the plurality of carbonyl-containing VOCs with a reactive chemical compound; quantifying each of the adducts of each of the plurality of carbonyl-containing VOCs to establish a subject value for each of the adducts; and comparing each subject value to a range of healthy specimen values for each of the adducts of the plurality of carbonyl-containing VOCs, the range of healthy specimen values corresponding to values calculated from healthy specimens, in order to determine the presence of at least three subject values at quantities greater than their respective range of healthy specimen values, thereby indicating a substantial likelihood of a lung cancer disease state in the subject specimen. Exemplary types of lung cancer suitable for detection using the methods described herein include, but are not limited to small cell lung cancer (SCLC), non-small cell lung cancer (NSCLC), squamous cell carcinoma, and adenocarcionoma.

In accordance with embodiments of the present invention, the plurality of carbonyl-containing VOCs is selected from the group consisting of 2-butanone, 2-hydroxyacetaldehyde, 3-hydroxy-2-butanone, 4-hydroxy-2-hexenal ("4-HHE"), 4-hydroxy-2-nonenal ("4-HNE"), and a mixture of $C_5H_{10}O$ compounds that includes 2-pentanone and pentanal.

As used herein, "healthy specimen" is defined as a specimen that does not have any pulmonary nodules (as indicated by CT scan) and does not have a diagnosable lung cancer disease state.

As used herein, "subject specimen" is defined as the specimen from which a sample of exhaled breath is obtained for the purpose of diagnosing or screening the presence/absence of a lung cancer disease state. The subject specimen may have been previously screened using a computerized tomography (CT), where a suspicious lesion or nodule was detected, and a higher specificity (true negative) test is favored that utilizes two or more, or three or more biomarker values above its respective threshold healthy specimen value. For screening purposes, the subject specimen may not have been screened using a CT scan, but may have other risk factors (e.g., smoking tobacco) and a higher selectivity (true positive) test is favored that utilizes one or more biomarker values above its respective threshold healthy specimen value.

As used herein, "threshold healthy specimen value" means a value determined by performing the testing method on a plurality of healthy specimens, wherein a subject value exceeding the determined threshold healthy specimen value indicates a lung cancer disease state.

As used herein, "substantial likelihood of a lung cancer disease state" means that the probability that the lung cancer disease state exists in the subject specimen is about 80% or more, based on the confidence levels of the testing method, whereas "likelihood of a lung cancer disease state" means that the probability that the lung cancer disease state exists in the subject specimen is about 50% or more, based on the confidence levels of the testing method. Of course, intermediate levels of likelihood are further contemplated, such as about 60% or more, or about 70% or more.

As used herein, "adducts" or "conjugates" denotes the reaction product of a reactive chemical compound and the carbonyl-containing VOCs lung cancer biomarker. These adducts are formed by a dehydration reaction of an aldehyde or a ketone, which transforms the volatile lung cancer biomarker into an unnatural, non-volatile chemical compound.

As previously noted above, breath analysis is a developing modality with potential to simplify the workup of suspected lung cancer. However, until the discovery of the present invention, no method has demonstrated clinical utility due to multiple factors, such as extremely low concentrations of involved carbonyl-containing VOC biomarker compounds, complexities in the isolation process of these compounds, and the lack of a diagnostic algorithm useful to clinicians. Previous reports of breath analysis of lung cancer patients have yielded a bewildering array of widely disparate compounds and profiles and the diagnostic utility of breath analysis has not been established. However, embodiments of the present invention are focused on select carbonyl-containing VOCs, such as 2-butanone, 2-hydroxyacetaldehyde, 3-hydroxy-2-butanone, 4-hydroxy-2-hexenal, 4-hydroxy-2-nonenal, and/or a mixture of $C_5H_{10}O$ compounds that includes 2-pentanone and pentanal.

In accordance with embodiments of the present invention, the method of detecting lung cancer includes the selective capture and concentration of certain lung cancer biomarkers, i.e., the carbonyl-containing VOCs, which may be achieved by passage of exhaled breath through a chemical preconcentrator assembly 10, which includes a chemical preconcentrator 15 having an inlet 17 and an outlet 19 that permit passage of the exhaled breath sample there through, as shown in FIG. 1. The assembly 10 further includes an inflatable polymeric film device 25 which may be fluidly coupled to a flowmeter 35 prior to the inlet 17 of the chemical preconcentrator 15. The outlet 19 of the chemical preconcentrator 15 may be fluidly coupled to a pressure gauge 40, a valve 45, and a vacuum pump 50, as described in more detail below.

One or more samples of exhaled breath from a subject specimen may be collected in the inflatable polymeric film device 25. One exemplary inflatable polymeric film device suitable for exhaled breath sample collection is a one liter Tedlar® gas sampling bag (Sigma-Aldrich Co., LLC, St. Louis, Mo.), which includes a Teflon® valve. For sample collection, the subjects may directly exhale into the Tedlar® gas sampling bag through the Teflon® valve, which provides a non-invasive collection technique.

The flow meter 35 is not particularly limited to any specific type of flow meter. Advantageously, the flow meter 35 should be capable of accurately measuring the volume of gas entering the chemical preconcentrator 15, which can permit quantifying the concentration of the carbonyl-containing VOCs in the exhaled breath samples.

The pressure gauge 40, the valve 45, and the vacuum pump 50 are similarly not particularly limited to any specific type. The vacuum pump 50 pulls a vacuum, which may be modulated or isolated from the chemical preconcentrator 15 by adjusting the valve 45. The pressure gauge 40 may be used to indicate proper functioning and/or operation of the vacuum pump 50 and the entire chemical preconcentrator assembly 10.

As noted above, the concentration levels of many biomarkers in exhaled breath are below detection limits of many standard analytical techniques. However, utilizing the chemical reactivity of the carbonyl functional group of aldehydes and ketones with certain reactive chemicals, the carbonyl-containing VOCs in exhaled breath can be preconcentrated prior to analysis. Accordingly, one suitable preconcentrator 15 useful for preconcentrating the carbonyl-containing VOCs in exhaled breath is described in U.S. Pat.

No. 8,663,581, which is incorporated herein in its entirety and further described herein. It should be appreciated that while the preconcentrator and methods embodied within the teachings of U.S. Pat. No. 8,663,581 were employed in embodiments of the present invention described herein, the invention is not particularly limited thereto. Other preconcentrator devices and/or methods may be utilized, so long as the devices and methods are effective in preconcentrating the requisite carbonyl-containing VOCs in exhaled breath to provide analytical samples.

Thus, in accordance with an embodiment, the chemical pre-concentrator 15 may include a support structure and a layer of a reactive chemical compound on a surface of the support structure. As used herein, the phrase "reactive chemical compound" includes molecular compounds held together by covalent bonds and salts held together by ionic bonds. The reactive chemical compound form conjugates or adducts with the carbonyl-containing VOCs in order to affect the collecting and pre-concentrating. As used herein, "carbonyl-containing" refers to aldehydes and ketones.

In general terms, the reactive chemical compounds include a reactive terminus capable of reacting with a carbonyl functional group on the VOC of interest; an anchoring moiety capable of reversibly effecting the formation of a layer on the surface of the support structure, and a linking group between the reactive terminus and the anchoring moiety. As represented in Formula (I) below, the reactive terminus includes an amino group ($NH_2$) bonded to a heteroatom (Z), a linking group (L), and an anchoring moiety (Y), wherein Z, L, and Y are defined below. In accordance with embodiments of the present invention The reactive chemical compound has a general formula according to that of Formula (I):

$$H_2N-Z-L-Y \qquad \text{Formula (I)}$$

wherein Z is NH, NR or O; L is a linking group; and Y is di-substituted or tri-substituted N or P moiety; R is selected from the group consisting of alkyls, aralkyls, aralkenyls, and aralkynyls, each of which may be substituted or unsubstituted, and optionally contain one or more heteroatoms.

According to an embodiment, Y can be $-NR^1R^2$, or $-NR^1R^2R^3$, $-PR^1R^2$, $-PR^1R^2R^4$, wherein $R^1$, $R^2$, $R^4$ are independently selected from the group consisting of alkyls, aralkyls, aralkenyls, and aralkynyls, each of which may be substituted or unsubstituted, and optionally contain one or more heteroatoms; and $R^3$ is selected from the group consisting of H, alkyls, aralkyls, aralkenyls, and aralkynyls, each of which may be substituted or unsubstituted, and optionally contain one or more heteroatoms. In an alternative embodiment, $R^1$ and $R^2$ in combination can also form a heterocyclic ring, such as a piperidine or a morpholine moiety.

According to another embodiment of the invention, the reactive chemical compound may include a reactive terminus, a cationic moiety and a linking group L therebetween. When Y is $-NR^1R^2R^3$ or $-PR^1R^2R^4$, the reactive chemical compound is a cationic salt, which may further comprise $^-A$, which is an anionic counter-ion. Accordingly, the cationic moiety may comprise a cationic nitrogen, such as an ammonium ion, or a cationic phosphorus, such as a phosphonium.

When Y is phosphorus, $R^1$, $R^2$ and $R^4$ may all be an aryl group, such as phenyl. When Y is nitrogen, $R^1$, $R^2$ and $R^3$ may be alkyls, each of which may be substituted or unsubstituted, and optionally contain one or more heteroatoms. In an alternative embodiment, when Y is nitrogen, $R^1$, $R^2$ may be alkyls, each of which may be substituted or unsubstituted, and optionally contain one or more heteroatoms, and $R^3$ may be H.

According to embodiments of the invention, the reactive terminus may comprise a hydrazine or aminooxy group. For example, Z may be nitrogen, such as NH or NR, thereby forming a hydrazine terminus. Alternatively, Z may be oxygen, thereby forming an aminooxy terminus. The hydrazine or aminooxy termini form the reactive functional group of the reactive chemical compounds, and as such, the aldehydes and ketones react with the hydrazine or the aminoooxy functional groups via a dehydration or condensation reaction. Accordingly, the reactive terminus of the reactive chemical and the carbonyl functionality of the VOC are complementary reactants to the condensation reaction that forms adducts of the carbonyl-containing VOC lung cancer biomarkers.

According to embodiments of the present invention, the conjugates or adducts formed between the reactive chemical compounds of formula (I) are hydrazones (when Z=N) or oximes (when Z=O). In either adduct form, the covalent bonding fixes the VOC to the anchoring moiety and thereby pre-concentrates the carbonyl-containing VOC lung cancer biomarkers prior to analysis.

In the reactive chemical compound, the linking group L covalently bonds the reactive terminus to the anchoring moiety. The reactive chemical compounds are not particularly limited by their linking group. However, increased substitution in the proximity of the reactive terminus may increase steric hindrance and thereby affect the reactivity of the compound. As such, varying the substitution may enable differentiation between aldehyde and ketone analytes, if desired. According to embodiments of the invention, the linking group may include a non-ionic segment, which may be a substituted or unsubstituted alkyl, a substituted or unsubstituted aryl, or an ether. For example, the linking group L may be ethyl, propyl, butyl, pentyl, hexyl, heptyl, or octyl segment. The linking group L may include an ether, such as polyethyleneglycol (PEG).

When the reactive chemical compound is a salt, the anionic member (A) of the reactive chemical compound is a negatively-charged species which counterbalances the positively-charged moiety. According to another embodiment, A may be a conjugate base of a strong acid. For example, A may be a halide such as bromide or chloride. According to another embodiment, A may be a conjugate base of a weak acid. For example, A may be a carboxylate such as benzoate. In one embodiment, Z is O, and Y is nitrogen, and the reactive chemical compound has a general formula according to that of Formula (II):

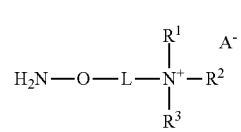

Formula (II)

where L, $R^1$, $R^2$, $R^3$, and A are defined above. In another embodiment, at least one of $R^1$, $R^2$ and $R^3$ is a methyl group and A is a halide.

It is also envisaged that the reactive chemical compound can include a plurality of reactive termini. For example, at least one of $R^1$, $R^2$ and $R^3$ may be a substituted or unsubstituted alkyl including at least two heteroatoms, and having a general formula of -L¹-Z—NH₂, wherein L¹ is a linking group between an ammonium nitrogen and Z.

As shown in Scheme 1, an exemplary reactive chemical compound (4), according to Formula (II) where L is ethyl, may be realized via a three step synthetic sequence. An amino alcohol (1) may be converted to the corresponding phthaloyl-protected aminooxy ammonium salt (3) by first treating the amino alcohol (1) with N-hydroxyphthalimide (2) under Mitsunobu conditions, which is subsequently followed by quaternization using an alkyl halide (R³—X) to provide the protected salt (3). Removal of the phthaloyl group via hydrazinolysis affords the reactive compound (4). Exemplary reactive chemical compounds are shown in Table 1 below.

Scheme 1: Synthesis of aminooxy reactive compound (4).

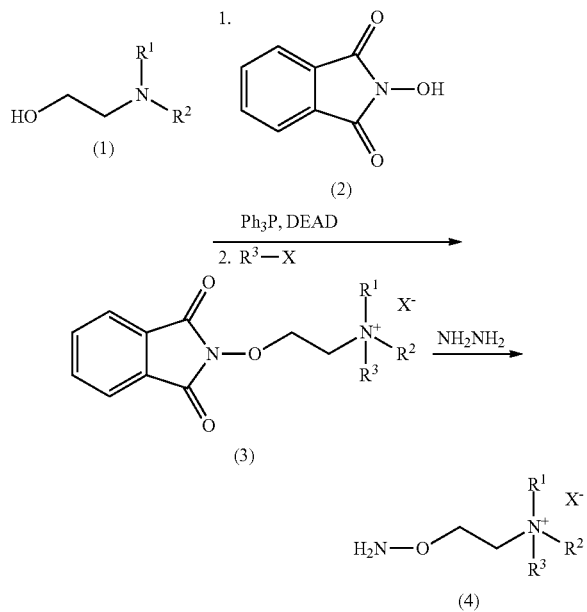

TABLE 1

Exemplary reactive chemical compounds 4a-4e prepared according to a three-step synthetic sequence.

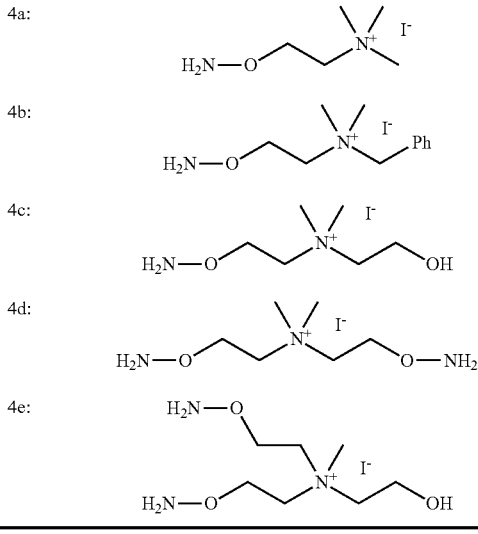

In yet another embodiment, Z is O, and Y is nitrogen, and the reactive chemical compound has a general formula according to that of Formula (III):

Formula (III)

The reactive chemical compounds in accordance with general Formula (III) can be prepared by omitting the quaternization step (2) in the synthetic sequence shown in Scheme I. For example, an exemplary reactive chemical compound according to Formula (III) where L is ethyl, may be realized via a two step synthetic sequence. Amino alcohol (1) may be converted to its corresponding phthaloyl-protected aminooxy by first treating the amino alcohol (1) with N-hydroxyphthalimide (2) under Mitsunobu conditions. Removal of the phthaloyl group via hydrazinolysis affords the tertiary amine reactive compound according for Formula (III). An exemplary tertiary amine reactive compound is N-(2-(aminooxy)ethyl)-morpholine (AMA).

According to an embodiment, the tertiary amine group can be used as an anchoring group. In an alternative embodiment, the tertiary amine reactive chemical compound may be converted to its Brønsted salt by treatment with a protic acid. For example, the tertiary amine reactive chemical compounds of Formula (III) can be dissolved in a suitable organic solvent and treated with an acid to prepare the reactive chemical compound of Formula (II), where R³ is H, and A is the conjugate base of the acid.

The reactive chemical compounds may be dissolved in one or more solvents and then deposited on a surface of a support structure. The solvent is not particularly limited, but should be capable of evaporating while leaving the reactive chemical compound on the surface of the support structure. Suitable solvents include polar protic solvents, polar aprotic solvents, or combinations thereof. Exemplary polar protic solvents include, but are not limited to, water and alcohols, such as methanol and/or ethanol. Exemplary polar aprotic solvents include, but are not limited to acetonitrile, dimethylformamide, dimethysulfoxide and nitromethane. The reactive chemical compound may be provided as a liquid, obtained by combining the reactive chemical compound and at least one solvent, which is then applied to a surface of a support structure. Removal of the solvent thereby deposits the reactive chemical compound on the surface of the support structure as a layer.

The support structures of the chemical pre-concentrators, in accordance with embodiments of the present invention, provide a surface to which the reactive chemical compound can be retained after solvent removal. A binding force that contributes to retaining the reactive chemical compound on the surface of the support structure is the interaction between the anchoring moiety (e.g., ammonium group) portion of the reactive chemical compound and the functional groups on the surface of the support structure, such as hydroxyls, as discussed further below.

The configuration of the support structure is not particularly limited by any specific configuration, but when present, features such as inlet and outlet structure, shapes and array patterns may affect the efficiency of the reactive chemical compound to capture the desired chemical analytes. Accordingly, the support structure may be configured to optimize surface area and flow dynamics.

Figure 2A:
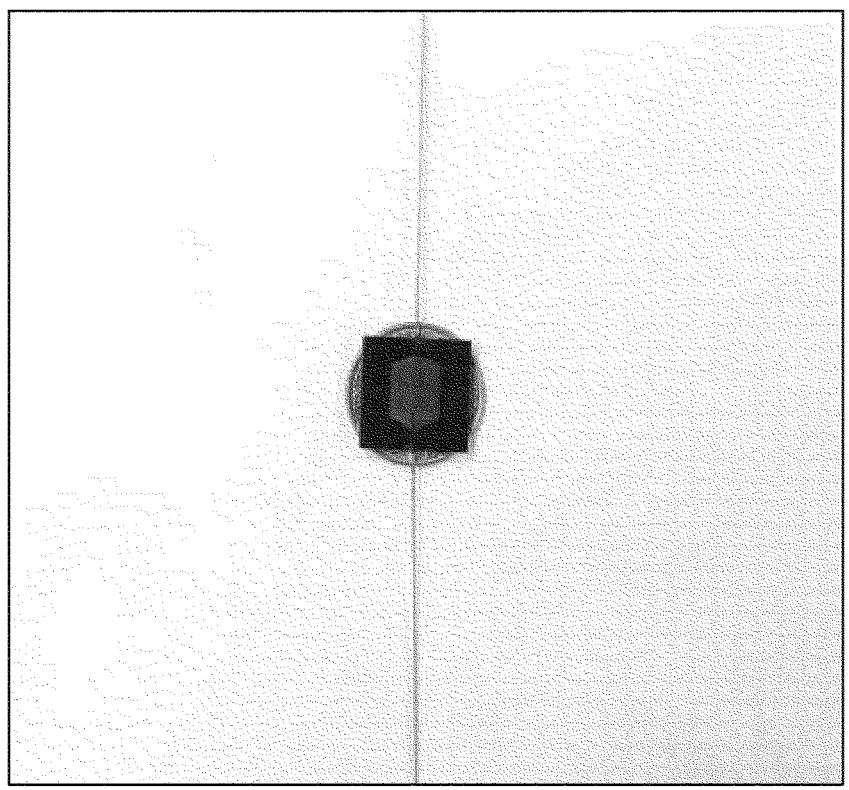
FIG. 2A is a photograph showing a preconcentrator connected to two fused silica tubes that is suitable for use in the schematic shown in FIG. 1; the preconcentrator is shown place on a U.S. dime to indicate its size.
Figure 2B:
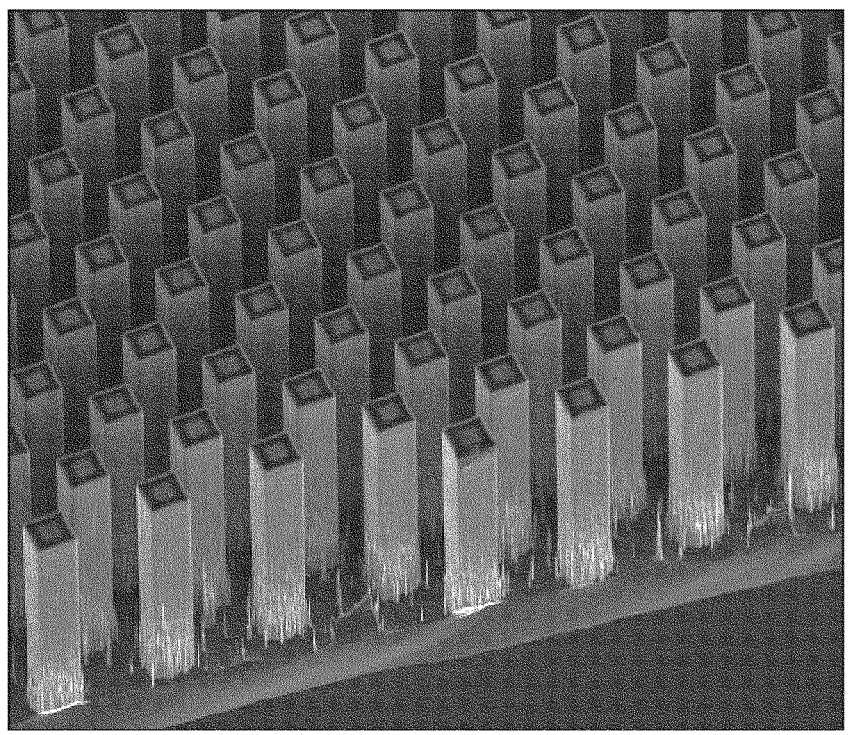
FIG. 2B is a scanning electron micrograph showing a micropillar array within the preconcentrator shown in FIG. 2A.

In reference to FIG. 2A, a photograph is provided showing a preconcentrator connected to two fused silica tubes, which is shown placed on a U.S. dime to indicate its size. In FIG. 2B, a scanning electron micrograph is provided showing a micropillar array within the preconcentrator shown in FIG. 2A. Other surface configurations of the pre-concentrator may be used.

The support structure may comprise any material that is compatible with the reactive chemical compound and is substantially insoluble in the solvent vehicle used to deposit the compound. More particularly, the surface of the support structure, which may be the same as or different from the underlying portion of the support structure, may comprise a material selected from the group consisting of dielectrics and semiconductors, which facilitates using MEMS techniques for manufacture. For example, the surface material may be silicon, polycrystalline silicon, silicon oxide, silicon nitride, silicon oxynitride, silicon carbide, titanium, titanium oxide, titanium nitride, titanium oxynitride, titanium carbide, aluminum, aluminum oxide, aluminum nitride, aluminum oxynitride, aluminum carbide, or combinations thereof. Advantageously, the reactive chemicals compounds show exceptional binding to support structure surfaces comprising silicon oxide, titanium oxide, aluminum oxide, or combinations thereof.

The surface of the support structure may affect the binding forces for adhering the reactive chemical compound to the support structure. For example, the thermal oxidation of the silicon surface of the wafer or the deposition of silicon dioxide may control the density of silanol groups and/or the electrostatic charge on the $SiO_2$ surface of the micropillars.

The chemical pre-concentrator 15 may further comprise a housing surrounding the support structure, wherein the housing has an inlet 17 and an outlet 19. According to an embodiment, the chemical pre-concentrator includes an airflow conduit directed at the surface of the support structure. Airflow conduits can include tubular devices, which are not attached to the support structure, or maybe fabricated into the support structure. The outlet 19 and/or the inlet 17 may be configured to couple with a sampling pump to thereby facilitate the transfer of a portion of a gaseous sample outside of the housing into the housing through the inlet.

The reactive chemical compound may be applied to the surface of the support structure by any suitable method. In one embodiment, a liquid comprising a first solvent and the reactive chemical compound is contacted with the surface of the support structure and the first solvent is removed by evaporation under reduced pressure. If desired, the first solvent may be evaporated in a vacuum oven. For example, a dilute solution of a reactive chemical compound can be prepared from about 3.5 mg of the reactive chemical compound dissolved in about 0.5 mL of a first solvent, which simply acts as a carrier solvent. About 10 µl to about 20 µl of the dilute solution is applied to the pre-concentrator, and then the first solvent is removed under reduced pressure to afford a loading of approximately 0.07 to 0.14 mg of the reactive chemical compound into the pre-concentrator. After the removal of the first solvent, the chemical preconcentrator is ready for concentrating the carbonyl-containing VOC biomarkers.

In practice, a measured volume of an exhaled breath sample is passed through the chemical preconcentrator and the carbonyl-containing VOCs form adducts with the reactive chemical, which are retained on the surface of the support structure, thereby effectively providing a concentrated sample of the adducts. After the exposure is discontinued, the chemical preconcentrator may be treated with a second solvent capable of dissolving the VOC adducts to facilitate removal of the VOC adducts from the surface of the support structure and provide a concentrated sample of the VOC adducts for analytical testing. Suitable solvents include polar protic solvents, polar aprotic solvents, or combinations thereof. Exemplary polar protic solvents include, but are not limited to, water and alcohols such as methanol. Exemplary polar aprotic solvents include, but are not limited to, acetonitrile, dimethylformamide, dimethysulfoxide and nitromethane. If desired, the eluted concentrated sample may be further concentrated by evaporating at least a portion of the second solvent.

At least a portion of the concentrated sample of the VOC adducts may be analyzed to identify and quantify the VOC adducts. One exemplary analytical tool is mass spectrometry, which may be performed with or without chromatography. For example, the conjugate may be analyzed using high performance liquid chromatography coupled with mass spectrometry (HPLC-MS) or gas chromatography coupled with mass spectrometry (GC-MS). Neutral chemical conjugates, such as those that can be obtained using tertiary amine reactive chemical compounds according to general Formula (III) are amenable to analysis using GC-MS. One beneficial feature of the tertiary amine reactive chemical compounds is their capability to be protonated with acid and form a positive charge, which is especially well-suited for analysis by Fourier transform ion cyclotron resonance-mass spectrometry (FT-ICR-MS), discussed below. By comparing FT-ICR-MS and GC-MS results, all ketones and aldehydes adducts can generally be identified and/or quantified. It should be appreciated that other analytical techniques, e.g., laser spectroscopy, etc., may also be useful toward quantifying the biomarker adducts. Internal standards may also be utilized to assist in the identification and/or quantification process.

Where the reactive chemical compound utilized is a cationic salt according to general Formula (II), another useful method of analyzing the conjugate is FT-ICR-MS. The cationic functionality also imparts exceptionally high sensitivity for [+] ion FT-ICR-MS using nanoelectrospray techniques. This exceptionally high sensitivity enables detection limits in the femtomole to attomole ranges. This sensitivity is orders of magnitude better than even the most sensitive GC-MS, which generally requires 100-1,000 femtomoles or more for detection. Moreover, because the VOCs are rendered non-volatile, the final analytical solution can be concentrated (e.g., to dryness) and taken up by a very small amount of solvent. Additionally, nanoelectrospray FTMS only needs a few microliters of sample volume.

Moreover, FT-ICR-MS may also be coupled with chemical ionization (CI) or photo ionization (PI) and operated in negative [−] ion mode. Operating in [−] ion mode, rejects the cationic phase and permits the analysis of other chemicals retained in the chemical pre-concentrator. In either mode, the VOC adducts of the reactive chemical compound may be desorbed from the structure support surface of the pre-concentrator by dissolution with solvent followed by direct FT-ICR-MS analysis.

The concentrated samples of the carbonyl-containing VOC adducts, which can be obtained from healthy subject controls, smoker subject controls, and subjects with benign pulmonary disease and early lung cancer, can be analyzed using FT-ICR-MS and quantified. The analytical results can then be compared between the subject groups using statistical methods, such as the Wilcoxon test to determine statistically significant differences between the subject groups. According to embodiments of this invention, specific carbonyl-containing VOC biomarkers (i.e., 2-butanone, 2-hydroxyacetaldehyde, 3-hydroxy-2-butanone, 4-hydroxy-2-hexenal, 4-hydroxy-2-nonenal, and a mixture of $C_5H_{10}O$ compounds that includes 2-pentanone and pentanal) have been identified to be present at statistically significant elevated levels in exhaled breath of lung cancer patients.

Herein we describe a quantitative analysis, using silicon microreactors chemical preconcentrators for the capture of carbonyl-containing VOCs, that forms adducts of the carbonyl-containing VOCs contained in exhaled breath, and the identification/quantification of specific carbonyl-containing VOCs that are related to lung cancer stages and histology. The method described herein only requires a subject patient to provide a sufficient quantity of exhaled breath, such as filling a one-liter Tedlar bag with exhaled breath. The exhaled breath sample can then be further processed and quantitatively analyzed, for example by mass spectrometry.

The methods described herein is premised on the believed principle that lung cancer induces oxidative stress and oxidase enzymes, and this in turn produces higher concentrations of specific carbonyl-containing VOCs in exhaled breath. Carbonyl-containing VOCs are produced in biochemical pathways as intermediates, and some can be unique to a given pathway, such as lipid oxidation induced by free radicals. Therefore, the investigation focused on identification of carbonyl-containing VOC lung cancer biomarkers in exhaled breath using the silicon microreactor chemical preconcentrator technology that we previously developed for capture and analysis of trace carbonyl VOC in air and exhaled breath.

Non-limiting examples of a method for detecting a lung cancer disease state, in accordance with the description, are now disclosed below. These examples are merely for the purpose of illustration and are not to be regarded as limiting the scope of the invention or the manner in which it can be practiced. Other examples will be appreciated by a person having ordinary skill in the art.

EXAMPLES

The Chemical Preconcentrator

The chemical preconcentrators (or silicon microreactors) were fabricated from 4"-silicon wafers using standard microelectromechanical systems (MEMS) fabrication techniques, such as described in Li, M. et al. (2012) *Preconcentration and Analysis of Trace Volatile Carbonyl Compounds, Anal. Chem.* 84:1288-1293 and U.S. Pat. No. 8,663,581. The microreactor (FIG. 2A) includes of an array of micropillars defining microfluidic channels (seen in FIG. 2B). The micropillars have a high-aspect-ratio with dimensions of 50 μm×50 μm×250 μm created by dry reactive ion etching (DRIE). The distance from center to center of the micropillars is 100 μm. The channel size is 7 mm×5 mm, with a total volume in the microreactor of about 5 μL. The microreactor includes over five thousand square micropillars corresponding to a total micropillar surface area of about 260 mm2. The inlet and outlet of the microreactor were fitted with 190 μm O.D., 100 μm I.D. deactivated fused silica tubes using a silica-based bonding agent (see FIG. 2A).

The surface functionalization of the channels and micropillars with 2-(aminooxy)-N,N,N-trimethylethanammonium (ATM) iodide (Structure 4a in Table 1) was performed by injecting ATM iodide in methanol solution of known concentration into the microreactor from one connection port followed by evaporation of the solvent under vacuum. The slightly negative surface charge of the silicon oxide micropillars allows for electrostatic binding of the cationic ATM on the surfaces of the micropillars. ATM reacts chemoselectively with trace carbonyl-containing VOCs in exhaled breath by means of oximation with high reactivity.

Exhaled Breath Specimen Collection and Processing

Air and exhaled breath samples were collected in one liter Tedlar® bags (Sigma-Aldrich, USA). The detailed research protocol for collection of exhaled breath samples was approved by the Institutional Review Board (IRB) at the University of Louisville. Exhaled breath samples of healthy smoker and non-smoker controls (n=88) and patient with pulmonary nodules (n=129) were analyzed and the concentrations of all carbonyl-containing compounds were determined. All clinical diagnosis of patients with pulmonary nodules were made after the collection of exhaled breath samples and the clinical diagnostic results of lung cancer and benign pulmonary were compared with the conclusions based on the analytical results of the exhaled breath samples.

For the sample collection of exhaled breath, subjects would directly exhale breath into Tedlar® bags through the Teflon® tip, thus providing a non-invasive collection technique that was readily accepted by the patients. After collection of exhaled breath, the Tedlar® bags were connected to the inlet port of the microreactor through one fused silica tube. The exit port of the microreactor was connected to a vacuum pump through the other fused silica tube on the microreactor as shown in FIG. 2A. The analysis assembly 10, shown in FIG. 1, for capture of carbonyl-containing VOCs includes a vacuum pump 50 to pull gaseous breath samples from the Tedlar® bag through the ATM-coated preconcentrator 15. After the exhaled breath sample had been pulled through the preconcentrator 15 and evacuated by vacuum, the preconcentrator 15 was disconnected. Finally, the ATM-VOC adducts were eluted from the preconcentrator 15 with 100 μL cold methanol to afford 99% ATM-VOC recovery. The eluted solution was directly analyzed by FT-ICR-MS. A known amount of ATM-acetone-d6 in methanol was added to the eluent as an internal standard. The concentrations of all carbonyl compounds in exhaled breath were determined by comparison of the relative abundance with that of added ATM-acetone-d6 as the internal standard reference.

FT-ICR-MS Instrumentation

The eluent was analyzed by a hybrid linear ion trap-FT-ICR-MS (Finnigan LTQ FT, Thermo Electron, Bremen, Germany) equipped with a TriVersa NanoMate ion source (Advion BioSciences, Ithaca, N.Y.) with an electrospray chip (nozzle inner diameter 5.5 μm). The TriVersa NanoMate was operated in positive ion mode by applying 2.0 kV with no head pressure. Initially, low resolution MS scans were acquired over 1 minute to ensure the stability of ionization, after which high mass accuracy data was collected using the FT-ICR analyzer. FT-MS scans were acquired for 8.5 min at a target mass resolution of 100,000 at 800 m/z. The AGC (automatic gain control) maximum ion time was set to 500 ms (but typically utilized <10 ms) and five "μscans" were acquired for each saved spectrum; thus the cycle time for each transformed and saved spectrum was about 10 seconds. FT-ICR mass spectra were exported as exact mass lists into a spreadsheet file using QualBrowser 2.0 (Thermo Electron), typically exporting all of the observed peaks. ATM and ATM-VOC adducts were assigned based on their accurate mass by first applying a small (typically <0.0005) linear correction based on the observed mass of the internal standard.

Statistical Data Analysis

The measured carbonyl VOC concentrations in exhaled breath samples were separated into healthy control, NSCLC, SCLC, and patient with benign pulmonary nodules groups. The NSCLC group was further separated into adenocarcinoma and squamous cell carcinoma subgroups and analyzed by the Wilcoxon test to determine statistically significant differences between the two groups. The Wilcoxon tests were performed using Minitab version 16.0.

Results and Discussion

The efficiencies of carbonyl capture by the ATM-coated preconcentrator were characterized first by using single carbonyl standards and mixtures of carbonyl standards. The capture efficiencies are affected by the velocity of the VOC mixture flowing through the preconcentrators, as well as the molar ratio of ATM/carbonyl compound. Capture efficiencies greater than 98% have been achieved for trace ketones and aldehydes under the optimized preconcentrator microstructure and operation conditions.

Prior to exhaled breath analysis, the concentrations of carbonyl VOCs from laboratory air, clinic room air, and street air samples were determined. Then, the concentrations of carbonyl VOCs in exhaled breath samples from 88 healthy controls (45 smokers, 43 non-smokers) and 147 patients with pulmonary nodules were measured. Carbonyl-containing VOCs from C1 (formaldehyde) to C12 in the exhaled breath samples of the healthy subjects and the patients with pulmonary nodules have been detected.

It was further demonstrated that the identified specific carbonyl-containing VOC biomarkers were not related to smoking. Moreover, it was demonstrated a high specificity and sensitivity for early lung cancer as differentiated from benign pulmonary disease. Furthermore, in comparison to PET scanning, similar sensitivity for the diagnosis of lung cancer was demonstrated but greater specificity in identifying benign disease instead of lung cancer, thereby potentially avoiding invasive procedures on patients who never had cancer.

Clinical relevancy was demonstrated in 147 subject patients and 88 healthy volunteers that were studied. A total of 107 subject patients had lung cancer and 40 had benign pulmonary disease. The FT-ICR-MS spectra of the first ten lung cancer patients were carefully reviewed and compared to the normal controls (i.e., healthy subject volunteers). In this sudy four carbonyl compounds, which were present at elevated levels in the lung cancer patients, were characterized as lung cancer biomarkers and further studied prospectively in the remaining patients. They were 2-butanone, 2-hydroxyacetaldehyde, 3-hydroxy-2-butanone, and 4-hydroxy-2-hexanal (4-HHE). Although, on average, these select four compounds were all significantly elevated in the cancer group compared to the healthy control population (P values each <0.0001), there was overlap in the range of values in the two groups.

Diagnosis of the 147 patients with pulmonary nodules was made by either biopsy or resection after the collection of breath samples. A pathologic diagnosis of lung cancer was confirmed in 107 patients, and benign nodules in 40 patients. Five patients were clinically diagnosed with benign pulmonary nodules based on the shrinkage of nodule size for at least six months after the collection of breath samples. The 107 lung cancer patients were comprised of 8 with SCLC, 97 with NSCLC, 1 combined small and non-small cell lung cancer, and 1 carcinoid tumor.

Figure 3:
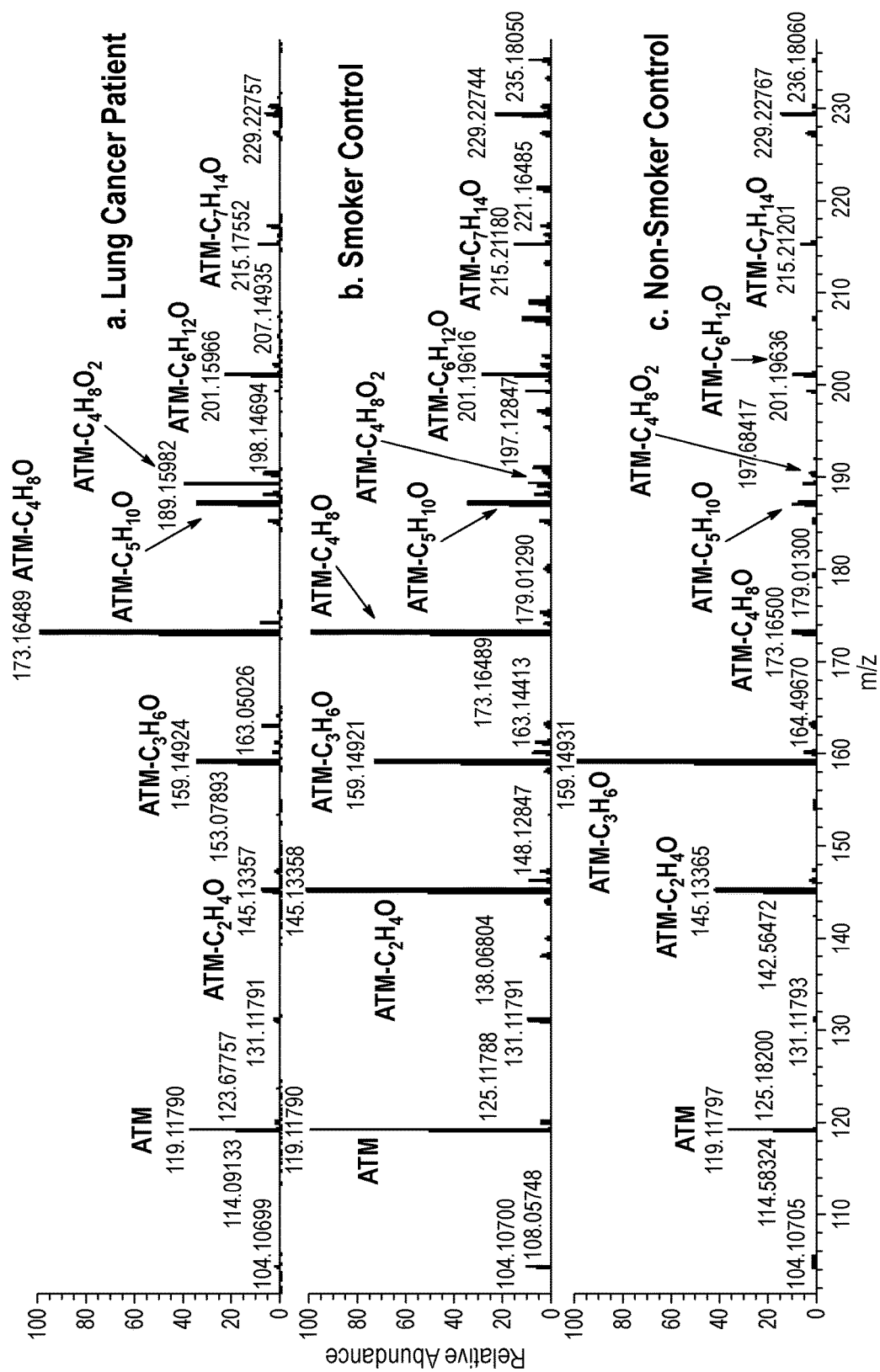
FIG. 3 is a comparison of three FT-ICR-MS spectra obtained by analysis of breath samples obtained from (a) lung cancer patient, (b) smoker control, and (c) non-smoker control.

The 2-butanone concentration (ATM-$C_4H_8O$ in FIG. 3A) typically is the highest of all carbonyl-containing VOCs in the exhaled breath of lung cancer patients. The acetaldehyde concentration (ATM-$C_2H_4O$ in FIG. 3B) is the highest among healthy smokers, likely due to its abundance in cigarette smoke. Healthy nonsmokers typically have acetone (ATM-$C_3H_6O$ in FIG. 3C) as the most concentrated carbonyl compound in their exhaled breath. FIG. 3 also shows that a lung cancer patient has obvious higher concentrations of 2-butanone and 3-hydroxy-2-butanone (ATM-$C_4H_8O_2$, Mw=189.15982) (FIG. 3A) than the healthy smoker (FIG. 3B) and nonsmoker (FIG. 3C). The Wilcoxon statistical test indicated that the concentrations of 2-butanone ($p<0.0001$), 3-hydroxy-2-butanone ($p<0.0001$), 2-hydroxyacetaldehye ($p<0.0001$), and 4-HHE ($p<0.0005$) were significantly higher in the exhaled breath samples of the group of lung cancer patients than in the healthy control group. The identified VOCs of lung cancer in exhaled breath samples were confirmed by FT-ICR-MS/MS using the same compounds ordered from Sigma-Aldrich and Cayman Inc. as standard references. The concentration ranges of these four VOCs for the group of the healthy controls, the group of the patients with lung cancer and the group of the patients with benign pulmonary nodules are presented in Table 2.

TABLE 2

| | Concentrations ranges of the four carbonyl-containing VOC biomarkers related to lung cancer | | | |
|---|---|---|---|---|
| VOCs (nmol/L) | Healthy controls | benign pulmonary | lung cancer patients | p* value |
| 2-Butanone | 0.45-2.34 | 0.79-4.25 | 1.78-8.38 | <0.0001 |
| 3-Hydroxy-2-butanone | 0.02-0.15 | 0.01-0.42 | 0.13-0.77 | <0.0001 |
| 2-Hydroxyacetaldehyde | 0.03-0.45 | 0.01-0.8 | 0.23-1.13 | <0.0001 |
| 4-Hydroxy-2-hexenal | 0.00007-0.009 | 0.00028-0.029 | 0.005-0.05 | <0.0005 | p*: all p values are between the group of healthy controls and the group of lung cancer patients.

There are overlaps for the concentration ranges of these four carbonyl-containing VOC lung cancer biomarkers. Notably, 2-butanone, 3-hydroxy-2-butanone, and 2-hydroxyacetaldehyde are present in ambient air. However, the concentrations of these three VOCs in air were at least 10 times lower than were found in exhaled breath. In addition, 4-HHE was not detected in air. The effects of tidal breath or environmental air on the concentrations of these carbonyl VOCs in exhaled breath samples can be neglected. Therefore, it was surmised that these carbonyl species are primarily from alveolar breath and their concentrations increase with cancer presence.

Table 3 lists the total number of the four carbonyl VOCs in the concentration ranges of lung cancer as shown in Table 2 for the 129 patients with pulmonary nodules. All patients (n=29) exhaling the four carbonyl VOCs at concentrations indicative of lung cancer were diagnosed with lung cancer while 34 out of 35 patients exhaling 3 carbonyl VOCs at concentrations indicative of lung cancer were diagnosed with lung cancer. There were two cancer patients without any of the four carbonyl VOCs at concentrations indicative of lung cancer. By defining a simple and practical diagnostic rule of an elevation of at least two of the four carbonyl VOCs as indicative of lung cancer, a sensitivity of 89.8% and a specificity of 81.3% was obtained. Although these results are very promising for clinical application, testing a much larger number of patients with pulmonary nodules in order to develop an even more reliable method for diagnosis of lung cancer could be advantageous.

TABLE 3

Total number of the carbonyl-containing VOC lung cancer biomarkers at concentration in the ranges of lung cancer shown in Table 2 in the breath samples of lung cancer (LC) and benign pulmonary nodule (BN) patients.

| No. of VOCs | 4 | 3 | 2 | 1 | 0 | all |
|---|---|---|---|---|---|---|
| No. of LC | 30 | 42 | 22 | 8 | 5 | 107 |
| No. of BN | 0 | 2 | 7 | 13 | 18 | 40 |

Figure 4A:
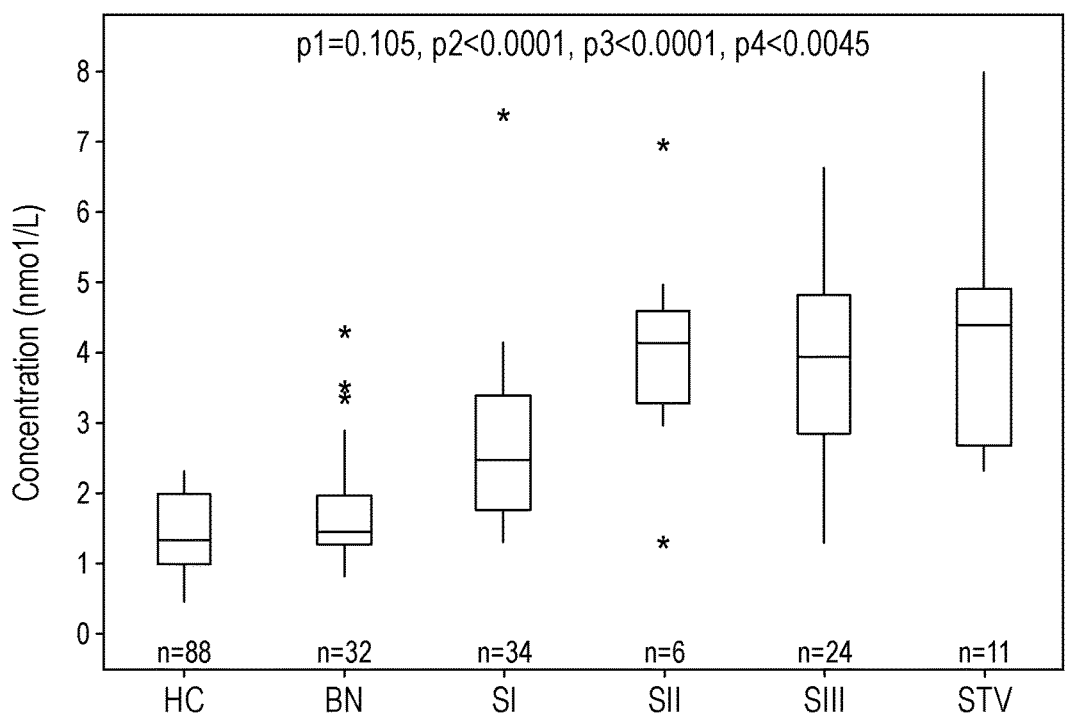
FIG. 4A is a box plot showing a relationship between 2-butanone in exhaled breath for subjects without cancer and subjects with NSCLC at various stages of disease progression.

To determine whether the carbonyl-containing VOC lung cancer biomarkers could be related to lung cancer stages, the concentrations of 2-butanone, 3-hydroxy-2-butanone, 2-hydroxyacetaldehyde, and 4-HHE in 34 patients with stage I, 16 patients with stage II, 24 patients with stage III, and 11 patients with stage IV of NSCLC were also analyzed by the Wilcoxon test. The concentrations of 3-hydroxy-2-butanone, 2-hydroxyacetaldehyde, and 4-HHE did not appear to be related to lung cancer stages. However, as shown in FIG. 4A, the concentration of 2-butanone can be related to stage I lung cancer. The concentration of 2-butanone in the exhaled breath samples of patients with stage I lung cancer was significantly higher than that in the healthy controls and the patients with benign pulmonary nodules, but lower than that in the patients with stages II to IV lung cancer. There does not appear to be a significant difference in 2-butanone concentrations in patients with stage II through IV lung cancer.

Figure 4B:
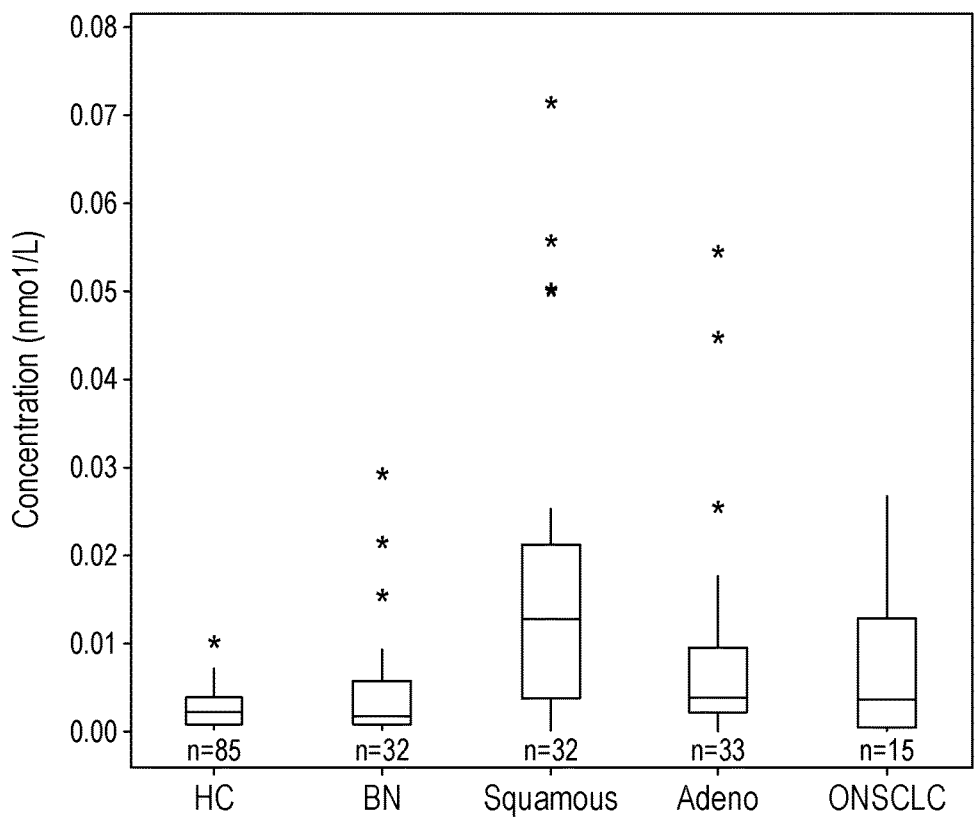
FIG. 4B is a box plot showing a relationship between 4-hydroxy-2-hexenal (4-HHE) in exhaled breath for subjects without cancer and subjects with different types of lung cancer.
Figure 6:
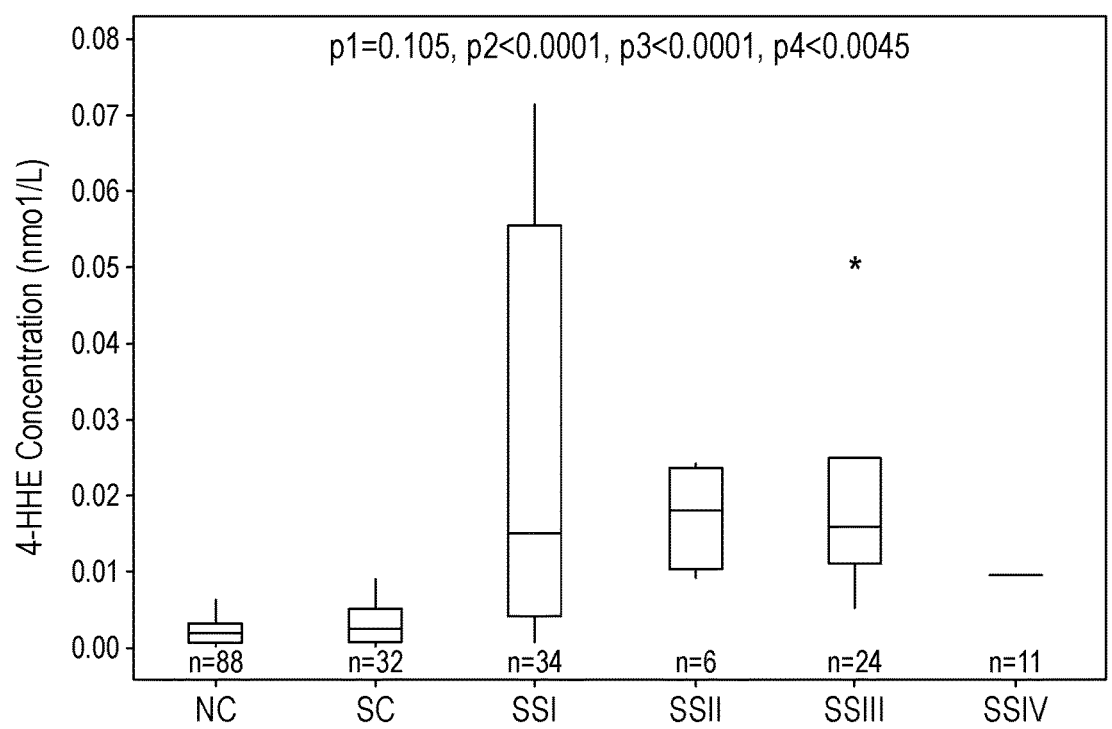
FIG. 6 is a box plot showing concentrations of 4-HHE in exhaled breath samples of nonsmoker subject controls (NS), smoker subject controls (SC) and the subjects with stage I (SSI) to stage IV (SSIV) of NSCLC.
Figure 7A:
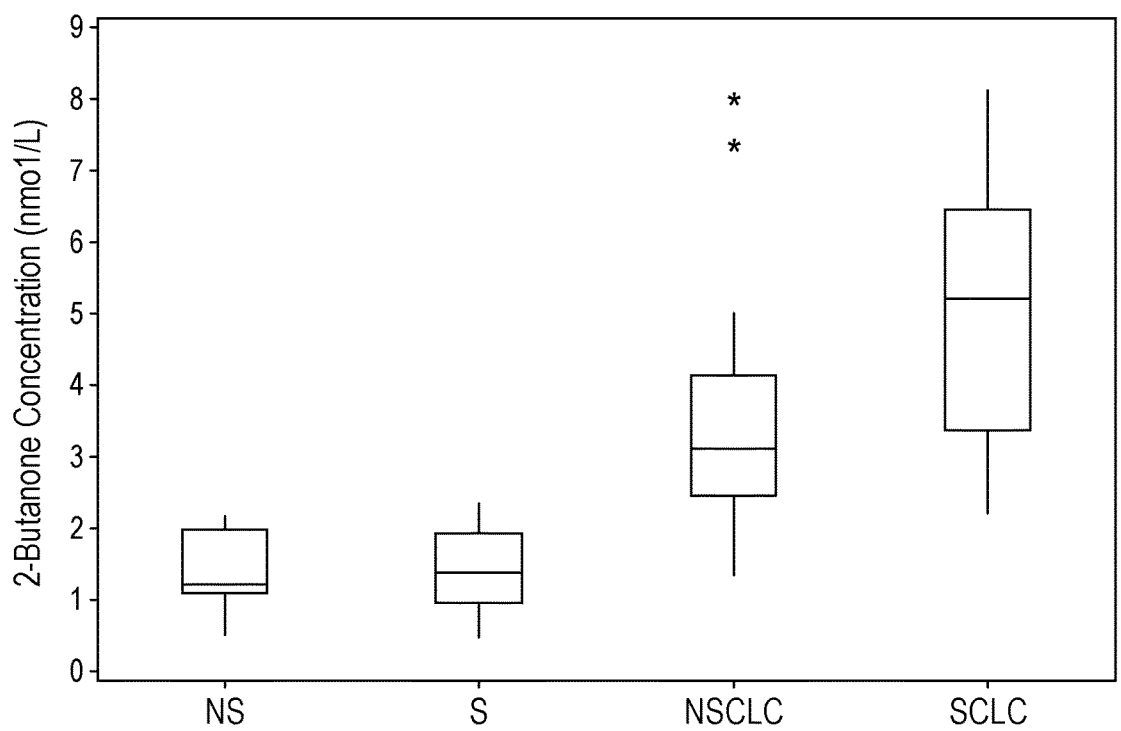
FIGS. 7A-7D are box plots showing concentrations 2-butanone (FIG. 7A), 3-hydroxy-2-butanone (FIG. 7B), 2-hydroxy-acetaldehyde (FIG. 7C), and 4-hydroxy-2-hexenal (FIG. 7D) in exhaled breath samples of nonsmoker subject controls (NS), smoker subject controls (S), and subjects with NSCLC and SCLC.
Figure 7B:
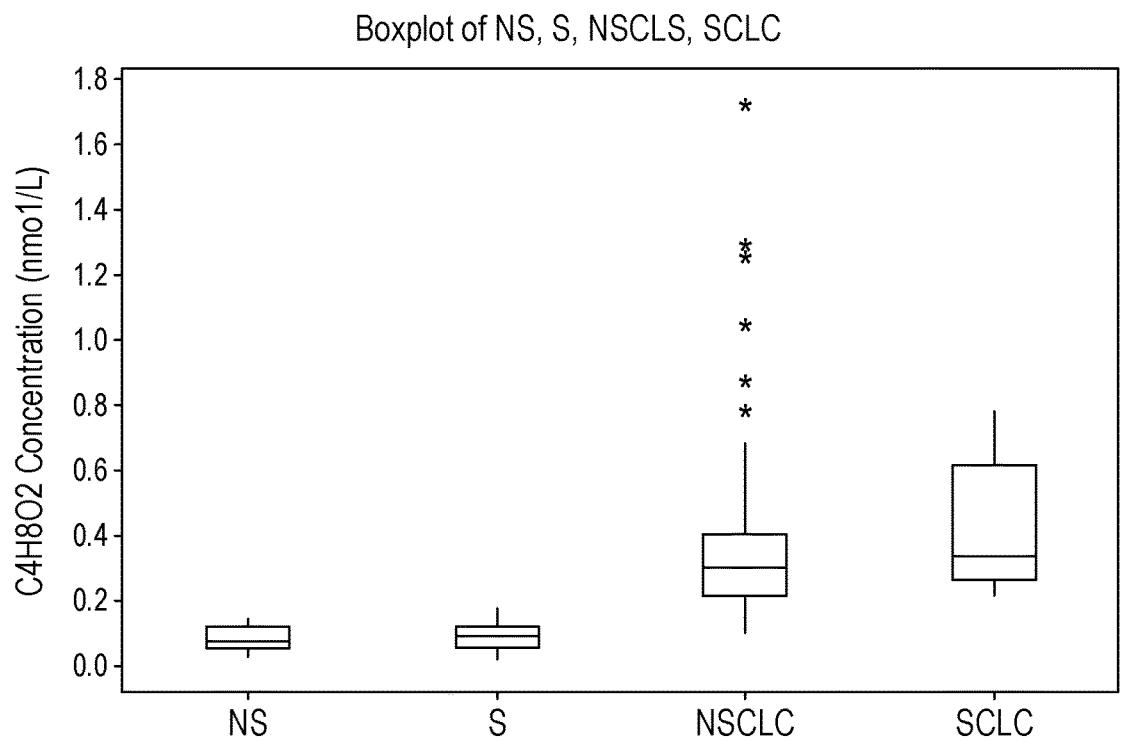
Figure 7C:
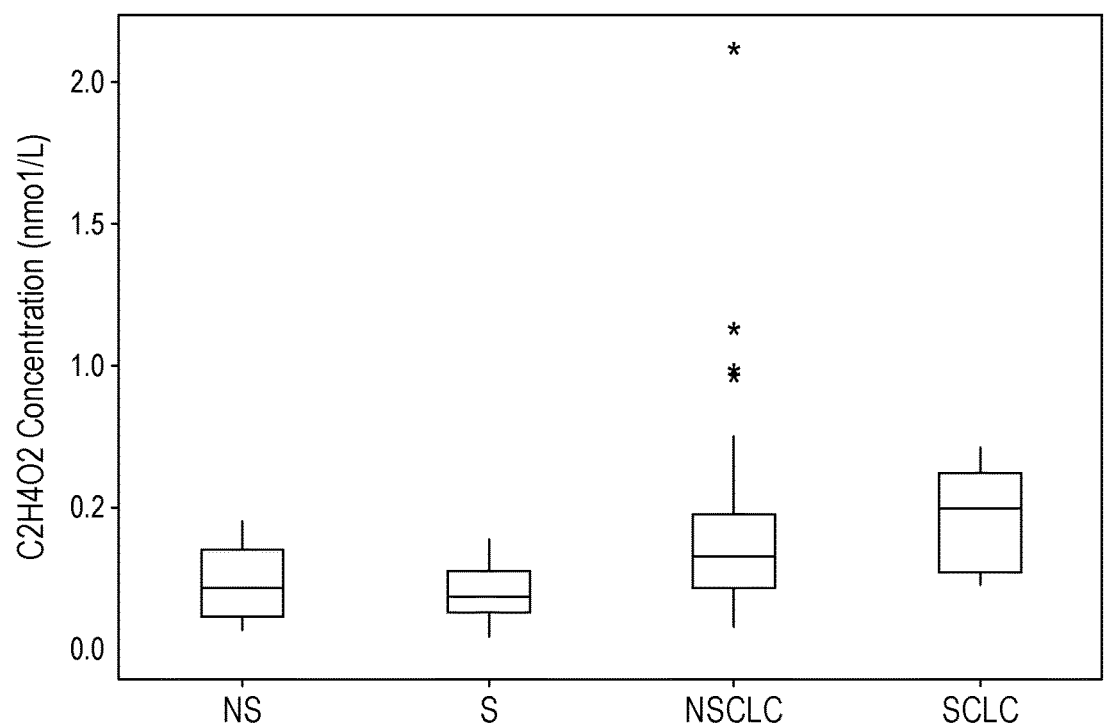
Figure 7D:
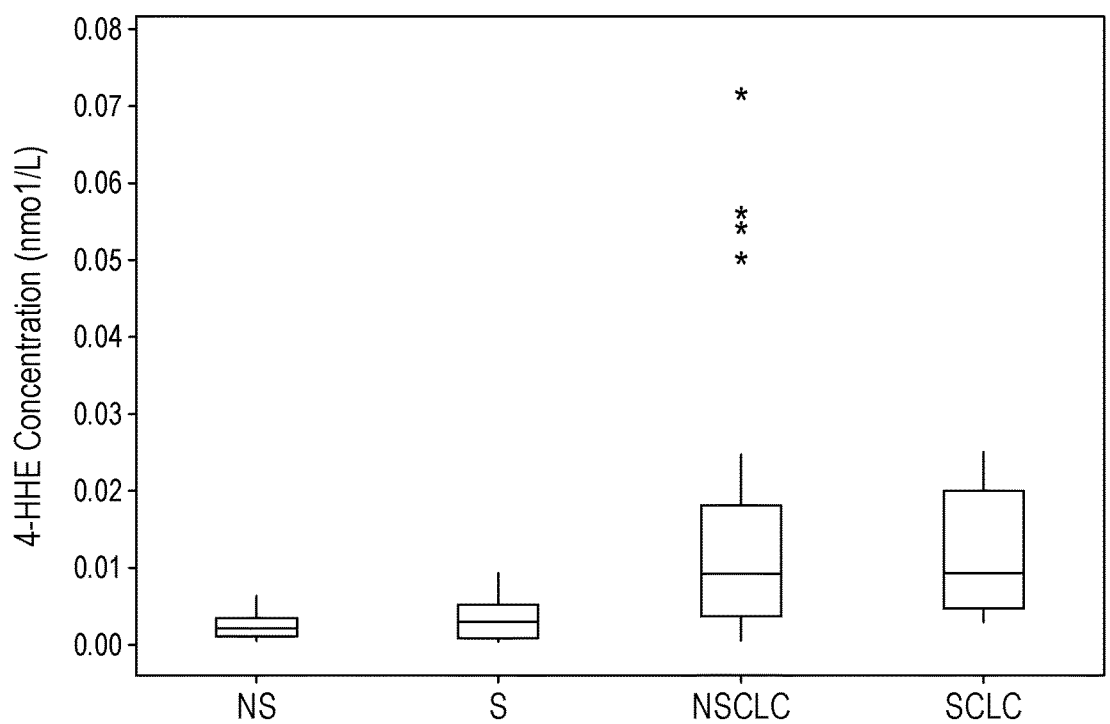

To determine potential existence of relationships between these carbonyl-containing VOC lung cancer biomarkers and the cancer histology of NSCLC, further analysis was performed for the concentrations of the four VOC biomarkers in 33 patients with adenocarcinomas, 32 patients with squamous cell carcinomas, and 15 patients with either poorly differentiated NSCLC or a combination of two types of NSCLC (labeled as ONSCLC in FIG. 4B). The patients with squamous cell carcinomas have significantly higher concentrations of 4-HHE than the patients with adenocarcinomas (p=0.03) (FIG. 4B). However, no significant difference was observed in the concentrations of 4-HHE between the group of adenocarcinomas and ONSCLC group. And no significant difference was observed in the concentrations of 4-HHE in the different stages of either adenocarcinoma or squamous cell carcinoma patients (FIG. 6).

Figure 5A:
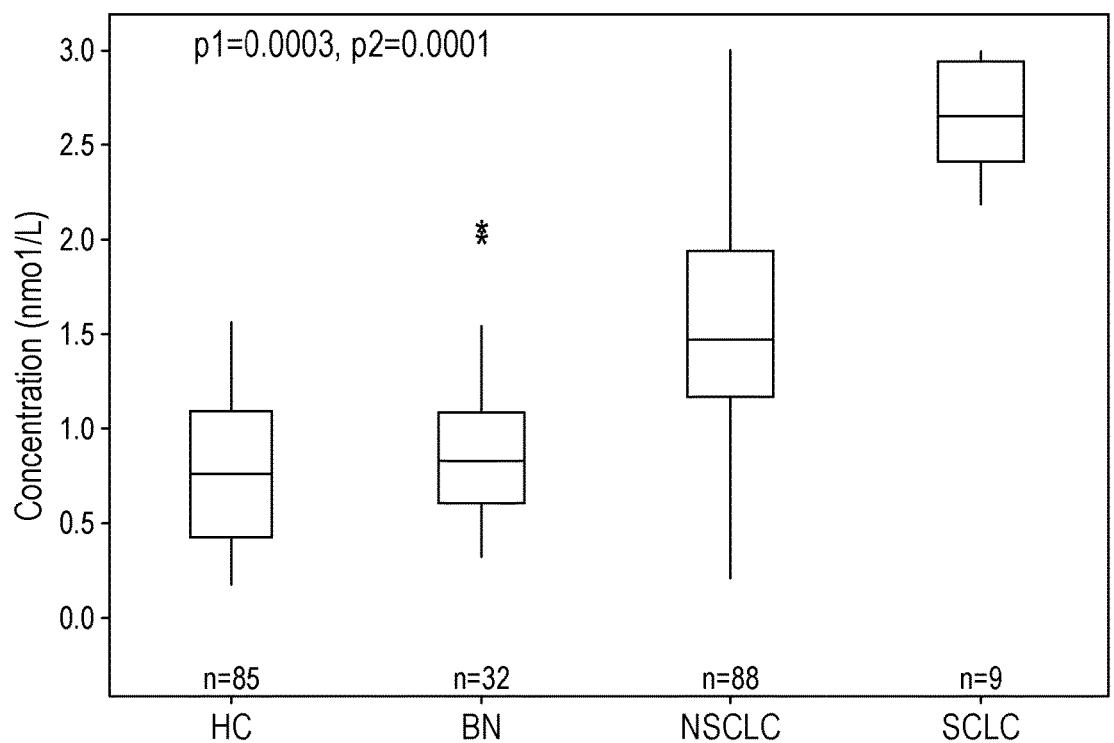
FIG. 5A is a box plot showing a relationship between $C_5H_{10}O$ (which includes 2-pentanone and pentanal) in exhaled breath for subjects without cancer and subjects with SCLC and NSCLC.
Figure 5B:
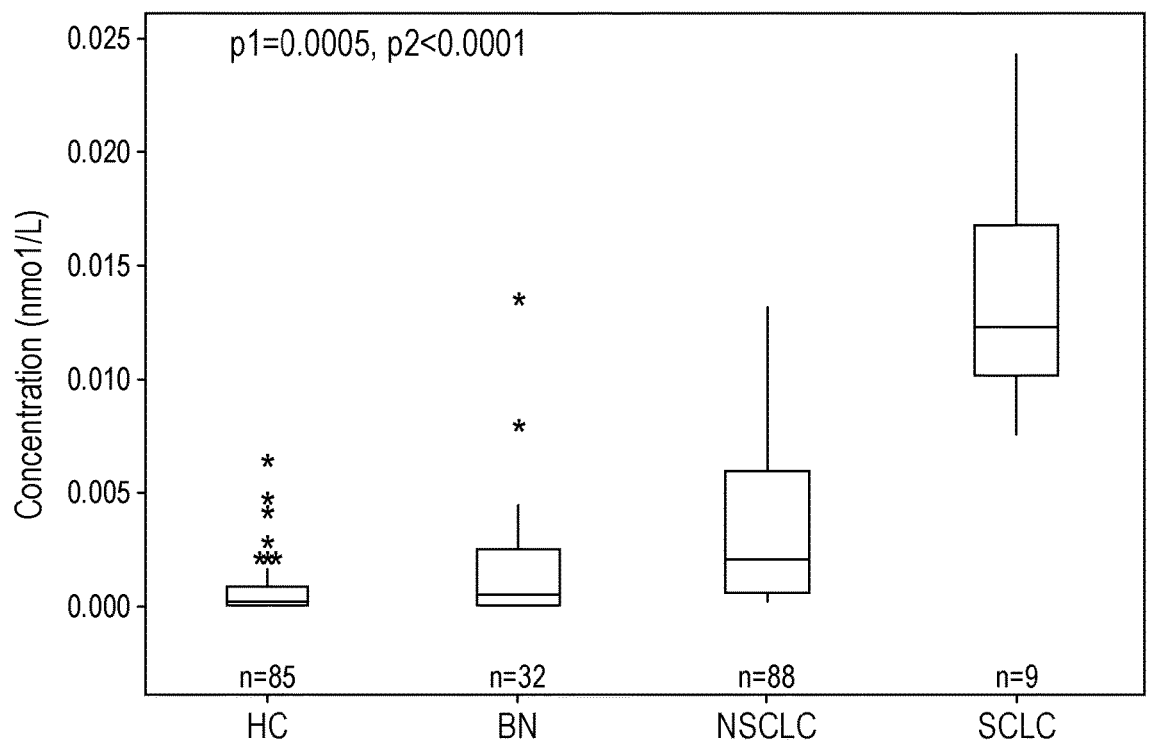
FIG. 5B is a box plot showing a relationship between 4-hydroxy-2-nonenal (4-HNE) in exhaled breath for subjects without cancer and subjects with SCLC and NSCLC.

In order to use breath analysis results for future diagnosis of patients with SCLC, the concentrations of all carbonyl VOCs in breath samples of 5 patients with limited stage SCLC and 4 patients with advanced stage SCLC were analyzed and compared with the patients (n=88) with NSCLC. There was no significant difference in the concentrations of 2-butanone, 3-hydroxy-2-butanone, 2-hydroxyacetaldehyde, and 4-HHE in the SCLC patients when compared to the NSCLC patient group (FIG. 7). However, FIG. 5 shows that there is a significant increase in the concentrations of 4-HNE (p<0.0001) and $C_5H_{10}O$ (p=0.0001) for the SCLC patients. GC-MS analysis was used to determine that $C_5H_{10}O$ in exhaled breath was a mixture of 2-pentanone and pentanal. 4-HNE is one of the most studied unsaturated aldehydes produced by lipid peroxidation and recent evidence has pointed to an inflammatory origin as a possible trigger of lung cancer development. Both 4-HHE and 4-HNE are recognized as products of lipid peroxidation, which could be induced by dysregulations of lung cancer. Accordingly, in addition to 2-butanone, 3-hydroxy-2-butanone, 2-hydroxyacetaldehyde, and 4-HHE, 4-HNE and $C_5H_{10}O$ may also be useful carbonyl-containing VOC biomarkers for diagnosing, staging, and/or identifying histology of lung cancer disease states.

Figure 8:
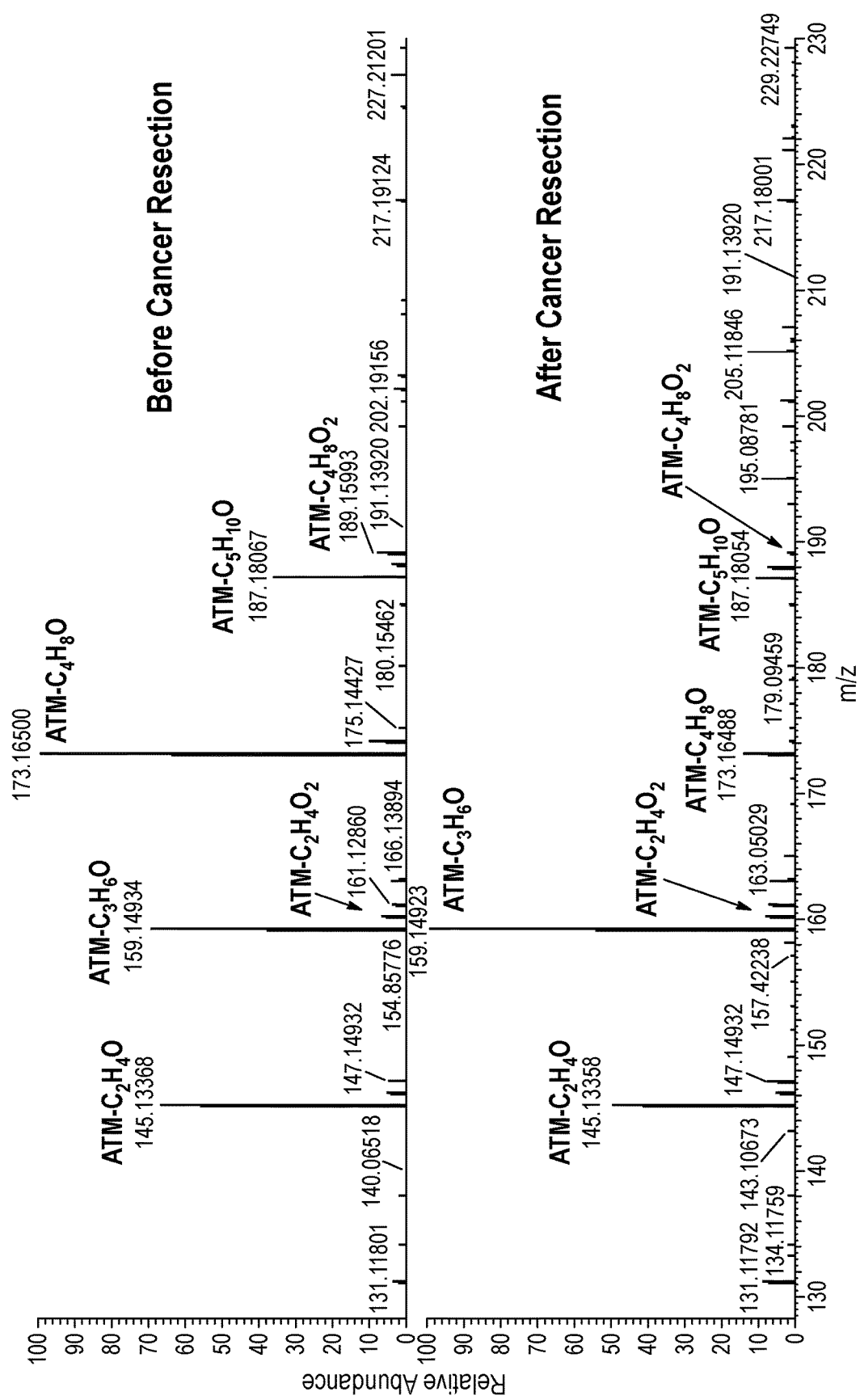
FIG. 8 is FT-ICR-MS spectra of breath samples from a lung cancer subject before and after resection of cancer.

To validate that elevated concentrations of 2-butanone, 3-hydroxy-2-butanone, 2-hydroxyacetaldehyde, and 4-HHE can be used for diagnosis of NSCLC in early stages (I and II), exhaled breath samples obtained from 15 patients with stage I and II NSCLC, before and after resection of the cancer, were analyzed and compared. Before resection, the profile of the carbonyl-containing VOC biomarker panel was that of a typical lung cancer patient (i.e., similar to FIG. 3A), and the concentrations of the noted VOCs were in the elevated ranges indicative of lung cancer. After cancer resection and a period of at least two weeks following the surgery, the VOC profile in exhaled breath was similar to that of healthy controls (as shown in FIG. 8), and the concentrations of the four VOC lung cancer biomarkers were in ranges of healthy controls.

In conclusion, using a silicon microreactor coated with ATM, four carbonyl-containing VOCs in exhaled breath have been identified that when at elevated concentrations reliably diagnose lung cancer. Specifically, the concentrations of 2-butanone, 3-hydroxy-2-butanone, 2-hydroxyacetaldehyde, and 4-HHE in breath are readily quantified by FT-ICR-MS analysis of the respective ATM-VOC adducts, and elevated concentrations of these adducts relative to concentrations in healthy patients, or even patients with benign pulmonary nodules, indicate the presence of lung cancer. The concentration of 2-butanone can be used to distinguish stage I lung cancer from stages II through IV. Furthermore, the concentration of 4-HHE may be used to distinguish squamous cell carcinoma from adenocarcinoma and other NSCLC, and the concentrations of 4-HNE and $C_5H_{10}O$ can be used to distinguish SCLC patients from NSCLC patients. These findings have immediate application as an accurate, noninvasive means for the diagnosis of lung cancer. Further study may show that they are an effective means of early detection of lung cancer in conjunction with CT scanning and in monitoring for the recurrence of lung cancer post resection.

A method for determining the risk of malignancy was derived by counting the number of elevated lung cancer biomarkers in a given patient. An elevated marker was defined as being higher than the range of the control population for that marker. The results between patients with benign disease and those with early and late stage cancer were compared. If three or four lung cancer biomarkers were elevated in the exhaled breath sample of the subject patient, there was about a 95% chance that the patient had cancer. Conversely, if none or only one of the lung cancer biomarkers was elevated, the probability of benign disease was 85%. Sensitivity and specificity were greater than 80%, if two, three, or four of the lung cancer biomarkers were elevated. These results were true and consistent for both early and late stage lung cancer. These results demonstrated that exhaled breath analysis could distinguish early lung cancer from benign disease that appear to be radiographically similar.

Moreover, comparing exhaled breath analysis (BA) to PET scan in the diagnosis of early stage lung cancer verses benign disease in 81 patients, breath analysis had similar sensitivity (83% BA, 90% PET) but greater specificity (74% BA, 39% PET). Thus, exhaled breath analysis was overall found to be more accurate than PET in the diagnosis of lung cancer.

Receiver Operator Characteristic (ROC) Analysis

Figure 9:
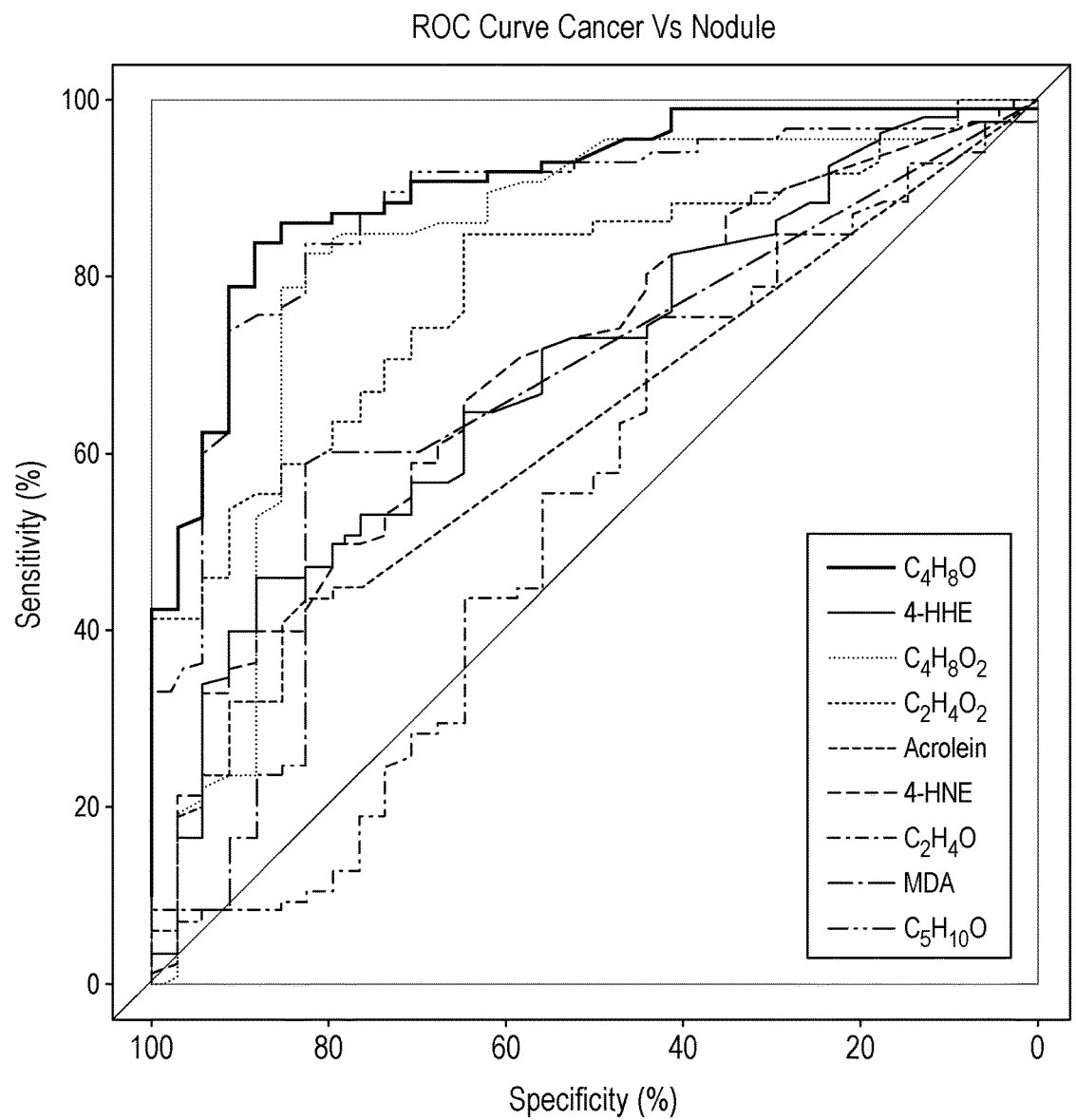
FIG. 9 is a receiver operator curve (ROC) analysis of nine carbonyl-containing VOCs for lung cancer vs benign pulmonary group.
Figure 10:
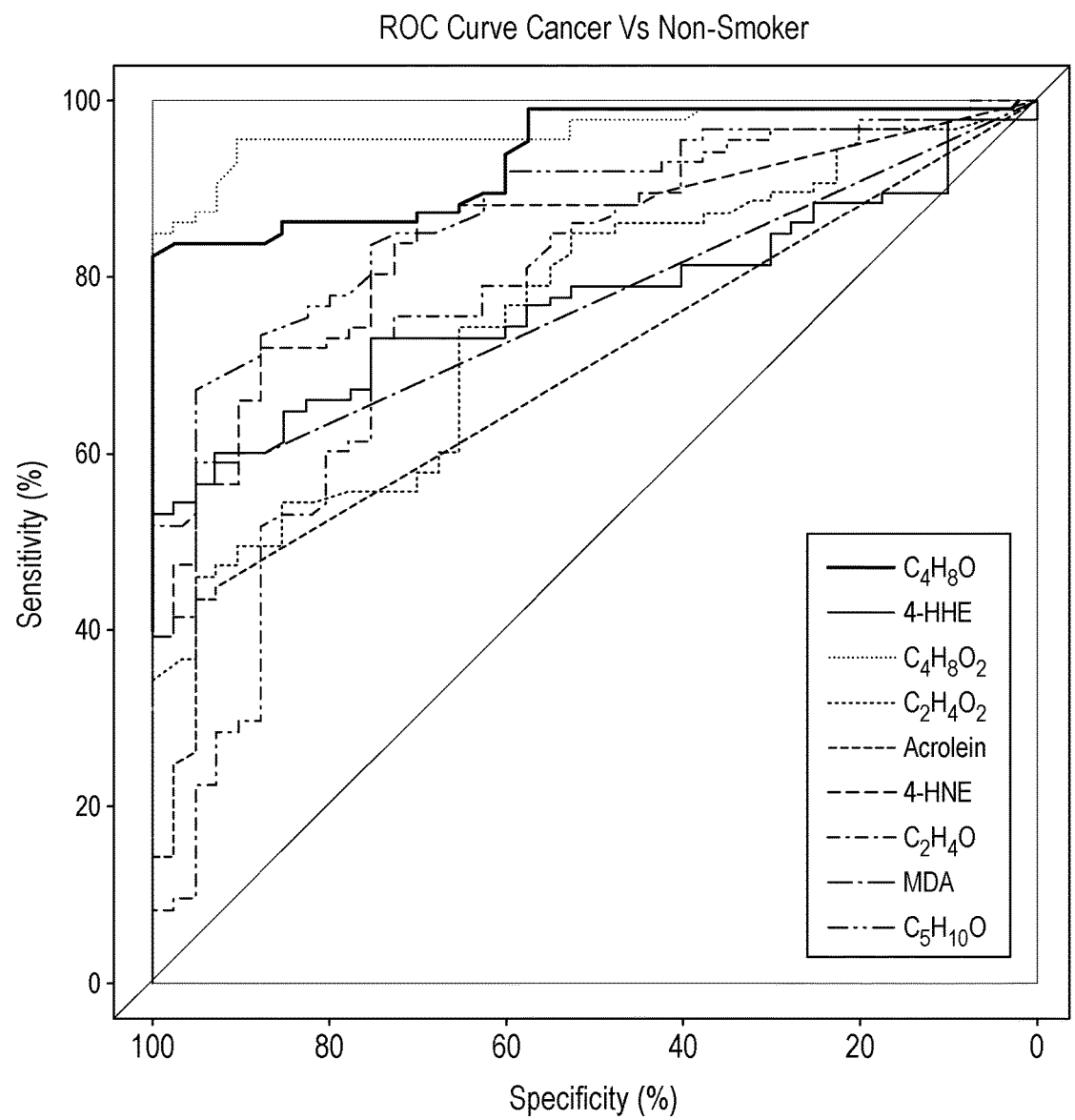
FIG. 10 is a ROC analysis of nine carbonyl-containing VOCs for lung cancer vs healthy non-smoker controls.
Figure 11:
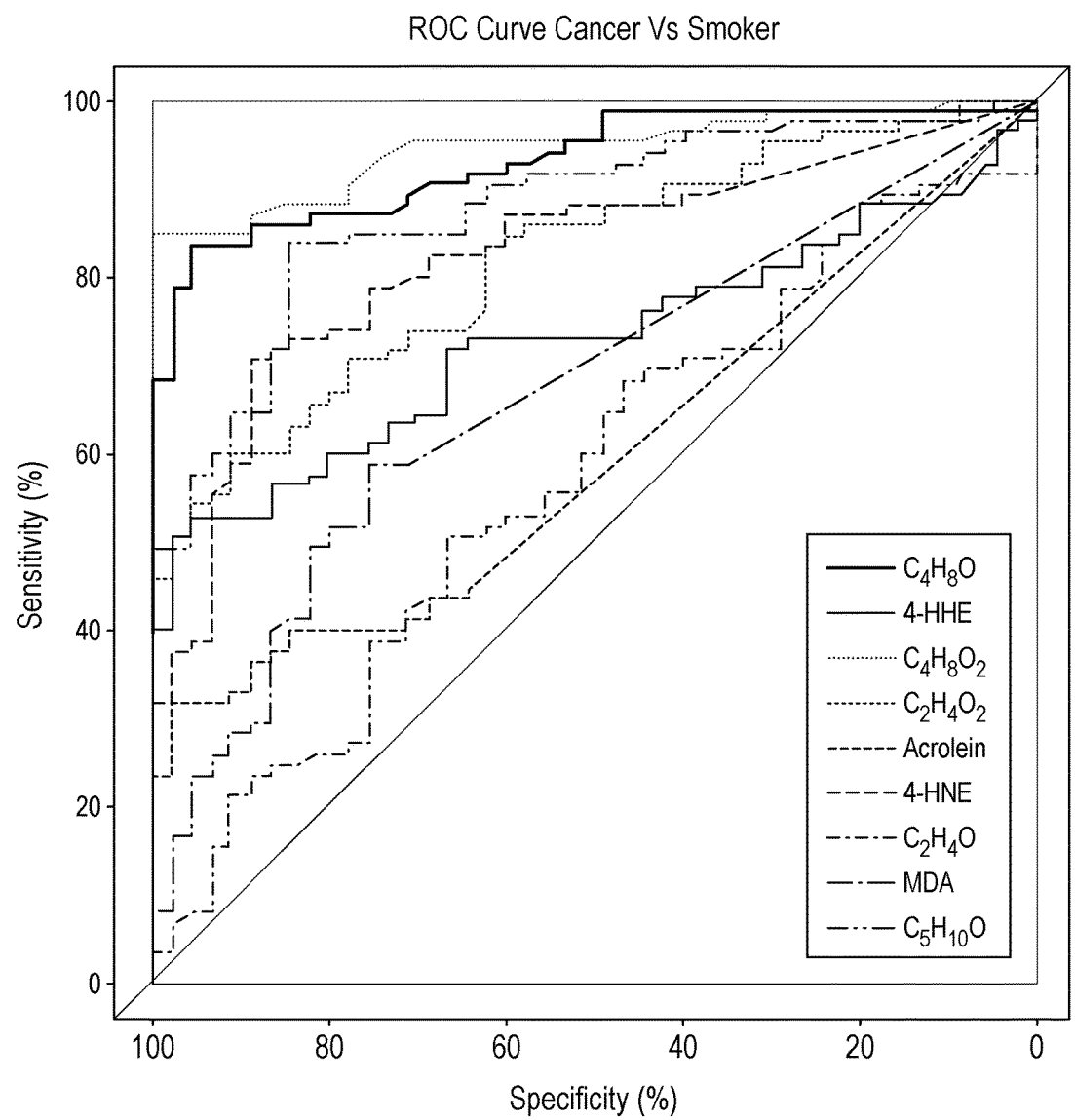
FIG. 11 is ROC analysis of nine carbonyl-containing VOCs for lung cancer vs healthy smoker controls.

FIGS. 9-11 show the receiver operator characteristic (ROC) curves of 9 carbonyl compounds detected in exhaled breath for distinguishing lung cancer patients against a comparison subject group. ROC curves are graphic representations of the relation existing between the sensibility and the specificity of a test, and it is generated by plotting the fraction of true positives out of the total actual positives versus the fraction of false positives out of the total actual negatives. In FIG. 9, the ROC curve is shown for the assessment of 107 patients with lung cancer as compared to 40 patients with benign pulmonary nodules. In FIG. 10, the ROC curve is shown for the assessment of 107 patients with lung cancer as compared to 43 healthy non-smoker controls. And in FIG. 11, the ROC curve is shown for the assessment of 107 patients with lung cancer as compared to 45 healthy smoker controls. There are various packages in R for creating ROC curves, but the results presented herein utilized Caret R package, version 5.15-023. (See Kuhn M. "Caret: Classification and Regression Training" R package version 5.15-023, 2012.) Sensitivity, specificity, overall accuracy, and area under the receiver operator characteristic (ROC) curve (AUC) are compared for 9 carbonyl compounds. Based on the present study, 2-butanone, a mixture of 2-pentanone and pentanal, and 3-hydroxy-2-butanone appear to show higher specificity for use as a single marker for distinguishing lung cancer patients from benign pulmonary nodule patients. 3-Hydroxy-2-butanone and 2-butanone achieve higher than 85% sensitivity and 80% specificity for distinguishing lung cancer from benign pulmonary nodules, non-smoker and smoker controls.

Table 4 provides threshold (cutoff) values (expressed in units of nanomole per liter of exhaled breath) for six of the nine carbonyl-containing VOC biomarkers that may be used for a single species screening for lung cancer. The sensitivities of the carbonyl-containing VOC biomarker are also shown. The confidence level (sensitivity for lung cancer) using 2-butanone and 3-hydroxy-2-butaone for screening lung cancer from non-smoker and smoker groups were about 85%. Using C5 carbonyl compounds (a mixture of pentanal and 2-pentanone), the sensitivity is about 80%, whereas the sensitivities of 2-hydroxyacetaldehyde, 4-hydroxy-2-hexenal, and 4-hydroxy-2-nonenal are about 62%, about 67%, and about 72%, respectively. The sensitivity and specificity are dependent on the cutoff (threshold) concentrations of each individual marker.

Thus in accordance with another embodiment of the present invention, a non-invasive method of screening for a lung cancer disease state in a subject specimen is provided. The method comprises detecting a level of one or more carbonyl-containing VOCs that are biomarkers for lung cancer in exhaled breath from the subject specimen, and identifying the subject specimen as having a greater than 60% likelihood of the lung cancer disease state if the level of one or more of the carbonyl-containing VOCs is elevated above its respective threshold value. As shown in Table 4, the sensitivity may be increased by using a different VOC biomarker. It should be further noted that in this study only 5 lung cancer subjects had no elevated biomarkers, whereas 102 lung cancer subjects had at least one elevated biomarkers listed in Table 4. According, screening a subject specimen for at least one elevated level of a biomarker selected from Table 4 showed a sensitivity of about 95%.

While the present invention has been illustrated by the description of embodiments, and while the illustrative embodiments have been described in considerable detail, it is not the intention of the inventors to restrict or in any way limit the scope of the appended claims to such detail. Additional advantages and modifications readily will appear to those skilled in the art. The invention in its broader aspects is therefore not limited to the specific details, representative apparatus and methods, and illustrative examples shown and described. Accordingly, departures may be made from such details without departing from the scope of the inventors' general inventive concept.

What is claimed is:

1. A non-invasive method of detecting or screening for a lung cancer disease state in a subject specimen, the method comprising the steps of:
    obtaining an exhaled breath sample from the subject specimen, wherein the exhaled breath sample includes one or more carbonyl-containing volatile organic compounds (VOCs), wherein the one or more carbonyl-containing VOCs is selected from the group consisting of 2-butanone, 2-hydroxyacetaldehyde, 3-hydroxy-2-butanone, 4-hydroxy-2-hexenal (4-HHE), 4-hydroxy-2-nonenal (4-HNE), and a mixture of $C_5H_{10}O$ compounds that includes 2-pentanone and pentanal;
    passing the exhaled breath sample through a chemical preconcentrator comprising a reactive chemical compound and reacting the one or more carbonyl-containing VOCs in the exhaled breath sample with the reactive chemical compound to form charged adducts of the one or more carbonyl-containing VOCs, wherein the reactive chemical compound has a general formula (I) of:

$$H_2N\text{---}Z\text{-L-Y}, \tag{I}$$

wherein Z is NH, NR or O; L is a Linking group; Y is a di-substituted or tri-substituted N or P moiety; R is

TABLE 4

Threshold concentrations of the six carbonyl-containing VOC for diagnosis and screening of lung cancer (n mol/L gaseous sample).

| | Chemical name | | | | | |
|---|---|---|---|---|---|---|
| | 2-butanone | 3-ydroxy-2-butanone | 2-Hydroxy acetaldehyde | 4-Hydroxy-2-hexenal | 4-Hydroxy-2-nonenal | Pentanone and pentanal |
| Formula | $C_4H_8O$ | $C_4H_8O_2$ | $C_2H_4O_2$ | $C_6H_{10}O_2$ | $C_9H_{16}O_2$ | $C_5H_{10}O_2$ |
| nmol/L | 2.34 | 0.167 | 0.391 | 0.009 | 0.0062 | 1.57 |
| Sensitivity | 85% | 85% | 62% | 67% | 72% | 80% | selected from the group consisting of alkyls, aralkyls, aralkenyls, and aralkynyls, each of which may be substituted or unsubstituted, and optionally contain one or more heteroatoms, and wherein the plurality of carbonyl-containing VOCs react with the reactive chemical compound via a condensation reaction to form adducts thereof;

quantifying one or more of the charged adducts of the one or more carbonyl-containing VOCs to establish a subject value for the one or more of the charged adducts; and comparing each subject value to a threshold healthy specimen value for the one or more of the charged adducts of the one or more carbonyl-containing VOCs, the threshold healthy specimen value corresponding to a value calculated from healthy specimens, in order to determine the presence of one or more subject values at quantities greater than their respective threshold healthy specimen values, thereby indicating a lung cancer disease state in the subject specimen.

2. The method of claim 1, wherein the lung cancer disease state is selected from the group consisting of small cell lung cancer (SCLC), non-small cell lung cancer (NSCLC), squamous cell carcinoma, and adenocarcinoma.

3. The method of claim 1, further comprising:
concentrating the one or more carbonyl-containing VOCs contained in exhaled breath samples obtained from a plurality of healthy specimens, wherein the one or more carbonyl-containing VOCs form charged adducts with the reactive chemical compound; and
quantifying the charged adducts of the one or more carbonyl-containing VOCs in the plurality of healthy specimens to establish the threshold healthy specimen values for each of the charged adducts of the one or more carbonyl-containing VOCs.

4. The method of claim 1, wherein obtaining the exhaled breath sample from the subject specimen comprises collecting the exhaled breath sample in an inflatable, polymeric film device to provide an inflated device comprising a breath sample; and wherein forming adducts of the plurality of carbonyl-containing VOCs with a reactive chemical compound comprises passing the breath sample through a chemical preconcentrator comprising the reactive chemical.

5. The method of claim 4, wherein passing the exhaled breath sample through a chemical preconcentrator comprises connecting the inflated device to an inlet of the chemical preconcentrator, and applying reduced pressure to an outlet of the chemical preconcentrator to induce flow of the exhaled breath sample from the inflated device through the chemical preconcentrator.

6. The method of claim 1, wherein Z is O, and Y is a di-substituted or tri-substituted nitrogen to provide the reactive chemical compound having a general formula (II)

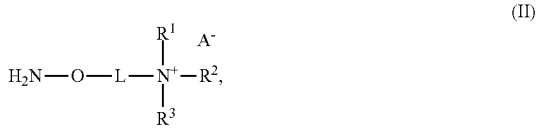

(II)

wherein $R^1$ and $R^2$ are independently selected from the group consisting of alkyls, aralkyls, aralkenyls, and aralkynyls, each of which may be substituted or unsubstituted, and optionally contain one or more heteroatoms, or wherein $R^1$ and $R^2$ in combination form a heterocyclic ring; $R^3$ is selected from the group consisting of H, alkyls, aralkyls, aralkenyls, and aralkynyls, each of which may be substituted or unsubstituted, and optionally contain one or more heteroatoms; and A is an anionic counter-ion; and wherein said Linking group L comprises a non-ionic segment selected from the group consisting of a substituted or unsubstituted alkyl, a substituted or unsubstituted aryl, and an ether.

7. The method of claim 1, wherein Z is O, and Y is a di-substituted nitrogen to provide the reactive chemical compound having a general formula (III)

(III)

wherein $R^1$ and $R^2$ are independently selected from the group consisting of alkyls, aralkyls, aralkenyls, and aralkynyls, each of which may be substituted or unsubstituted, and optionally contain one or more heteroatoms, or wherein $R^1$ and $R^2$ in combination form a heterocyclic ring.

8. The method of claim 1, wherein the reactive chemical compound is a 2-(aminooxy)-N,N,N-trimethylethanammonium salt.

9. The method of claim 1, wherein quantifying the charged adducts of the one or more carbonyl-containing VOCs to establish the subject value for each member of the charged adducts of the one or more carbonyl-containing VOCs comprises analyzing the charged adducts of the one or more carbonyl-containing VOCs using a mass spectrometer.

10. The method of claim 9, wherein the mass spectrometer uses Fourier-transform ion cyclotron resonance mass spectrometry (FT-ICR-MS).

11. The method of claim 9, wherein the mass spectrometer is coupled with a chromatography apparatus.

12. The method of claim 1, wherein the one or more carbonyl-containing VOCs comprises 4-HNE and a mixture of $C_5H_{10}O$ compounds that includes 2-pentanone and pentanal, the method further comprising:
distinguishing a SCLC disease state from a NSCLC disease state in the subject specimen by determining
a) a subject value of a 4-HNE adduct of the reactive chemical compound,
b) a subject value of $C_5H_{10}O$ adducts of the reactive chemical compound, or
c) both a) and b);
and comparing the subject value of a), b), or c) with a concentration range of the respective adduct indicative of at least one of the SCLC disease state and the NSCLC disease state in the subject.

13. The method of claim 12, further comprising:
d) identifying a concentration range for the 4-HNE adduct of the reactive chemical compound indicative of SCLC, and a concentration range for the 4-HNE adduct of the reactive chemical compound indicative of NSCLC;
e) identifying a concentration range for $C_5H_{10}O$ adducts of the reactive chemical compound indicative of SCLC, and a concentration range for $C_5H_{10}O$ adducts of the reactive chemical compound indicative of NSCLC; or
f) both d) and e).

14. The method of claim 1, wherein the one or more carbonyl-containing VOCs comprises 4-HHE, the method further comprising:

distinguishing between squamous cell carcinoma, adenocarcinoma, and NSCLC disease states in the subject specimen by determining
a) a subject value of a 4-HHE adduct of the reactive chemical compound
and comparing the subject value of a) with a concentration range of the respective adduct indicative of at least one of the squamous cell carcinoma disease state, the adenocarcinoma disease state, and the NSCLC disease state in the subject.

15. The method of claim 14, further comprising:
b) identifying a concentration range for the 4-HHE adduct of the reactive chemical compound indicative of squamous cell carcinoma, a concentration range for the 4-HHE adduct of the reactive chemical compound indicative of adenocarcinoma, and a concentration range for the 4-HHE adduct of the reactive chemical compound indicative of NSCLC.

16. The method of claim 1, wherein the one or more carbonyl-containing VOCs comprises 2-butanone, the method further comprising:
distinguishing a stage I lung cancer disease state from stages II-IV in the subject specimen by determining
a) a subject value of a 2-butanone adduct of the reactive chemical compound
and comparing the subject value of a) with a concentration range of the respective adduct indicative of at least one of the stage I lung cancer disease state and the stages II-IV disease state in the subject.

17. The method of claim 16, further comprising:
b) identifying a concentration range for the 2-butanone adduct of the reactive chemical compound indicative of the stage I lung cancer disease state.

18. A non-invasive method of screening for a lung cancer disease state in a subject specimen, the method comprising the steps of:
concentrating one or more carbonyl-containing volatile organic compounds (VOCs) contained in exhaled breath obtained from the subject specimen by mixing the one or more carbonyl-containing VOCs with a reactive chemical compound to form charged adducts of the one or more carbonyl-containing VOCs, wherein the one or more carbonyl-containing VOCs is selected from the group consisting of 2-butanone, 2-hydroxyacetaldehyde, 3-hydroxy-2-butanone, and 4-hydroxy-2-hexenal, 4-hydroxy-2-nonenal, and a mixture of $C_5H_{10}O$ compounds that includes 2-pentanone and pentanal and further wherein the reactive chemical compound has a general formula (I) of:

$$H_2N-Z-L-Y, \quad (I)$$

wherein Z is NH, NR or O; L is a Linking group; Y is a di-substituted or tri substituted N or P moiety; R is selected from the group consisting of alkyls, aralkyls, aralkenyls, and aralkynyls, each of which may be substituted or unsubstituted, and optionally contain one or more heteroatoms, and wherein the one or more carbonyl-containing VOCs react with the reactive chemical compound via a condensation reaction to form adducts thereof;
quantifying one or more of the charged adducts of the one or more carbonyl-containing VOCs to establish a subject value for each member of the one or more of the charged adducts of the one or more carbonyl-containing VOCs; and
comparing the subject value for each member of the one or more of the charged adducts of the one or more carbonyl-containing VOCs to a threshold healthy specimen value for each member of the one or more of the charged adducts of the one or more carbonyl-containing VOCs to determine the presence of one or more carbonyl-containing VOCs at quantities greater than its respective threshold healthy specimen value thereby indicating a substantial likelihood of the lung cancer disease state in the subject specimen.

19. A non-invasive method of detecting or screening for a lung cancer disease state in a subject specimen, comprising:
detecting levels of one or more carbonyl-containing volatile organic compounds (VOCs) selected from the group consisting of 2-butanone, 2-hydroxyacetaldehyde, 3-hydroxy-2-butanone, 4-hydroxy-2-hexenal, 4-hydroxy-2-nonenal, and a mixture of $C_5H_{10}O$ compounds that includes 2-pentanone and pentanal in exhaled breath from the subject specimen, and diagnosing the subject specimen as having a likelihood of the lung cancer disease state if the level of the detected one or more of the carbonyl-containing VOCs selected from the group consisting of 2-butanone, 2-hydroxyacetaldehyde, 3-hydroxy-2-butanone, 4-hydroxy-2-hexenal, 4-hydroxy-2-nonenal, and a mixture of $C_5H_{10}O$ compounds that includes 2-pentanone and pentanal is elevated above its respective threshold healthy specimen value, wherein detecting levels of the one or more carbonyl-containing VOCs comprises:
reacting the one or more carbonyl-containing VOCs with a reactive chemical compound to form charged adducts of the one or more carbonyl-containing VOCs, wherein the reactive chemical compound has a general formula (I) of:

$$H_2N-Z-L-Y, \quad (I)$$

wherein Z is NH, NR or O; L is a Linking group; Y is a di-substituted or tri substituted N or P moiety; R is selected from the group consisting of alkyls, aralkyls, aralkenyls, and aralkynyls, each of which may be substituted or unsubstituted, and optionally contain one or more heteroatoms, and wherein the one or more carbonyl-containing VOCs react with the reactive chemical compound via a condensation reaction to form adducts thereof;
quantifying one or more of the charged adducts of the one or more carbonyl-containing VOCs; and
correlating the quantified values for the one or more of the charged adducts of the one or more carbonyl-containing VOCs with the level of one or more carbonyl-containing VOCs in the subject specimen.

20. The method of claim 1 wherein the one or more carbonyl-containing VOCs is a plurality of VOCs.

21. The method of claim 18 wherein the one or more carbonyl-containing VOCs is a plurality of VOCs.

22. The method of claim 19 wherein the one or more carbonyl-containing VOCs is a plurality of VOCs.

* * * * *